(12) United States Patent
Voss et al.

(10) Patent No.: US 9,938,089 B2
(45) Date of Patent: Apr. 10, 2018

(54) AUTOMATED POSITIVE PRESSURE SOLID PHASE EXTRACTION APPARATUS AND METHOD

(71) Applicants: Garrett Voss, Reno, NV (US); Harrison Elings, Reno, NV (US)

(72) Inventors: Garrett Voss, Reno, NV (US); Harrison Elings, Reno, NV (US)

(73) Assignee: Hamilton Company, Reno, NV (US)

(*) Notice: Subject to any disclaimer, the term of this patent is extended or adjusted under 35 U.S.C. 154(b) by 0 days.

(21) Appl. No.: 14/598,876

(22) Filed: Jan. 16, 2015

(65) Prior Publication Data
US 2016/0009503 A1    Jan. 14, 2016

Related U.S. Application Data

(60) Provisional application No. 61/928,873, filed on Jan. 17, 2014.

(51) Int. Cl.
| | |
|---|---|
| *G01N 35/02* | (2006.01) |
| *B65G 47/82* | (2006.01) |
| *B01D 11/02* | (2006.01) |
| *G01N 35/10* | (2006.01) |
| G01N 35/00 | (2006.01) |
| G01N 1/40 | (2006.01) |

(52) U.S. Cl.
CPC .......... *B65G 47/82* (2013.01); *B01D 11/0207* (2013.01); *G01N 35/109* (2013.01); *G01N 35/0099* (2013.01); *G01N 2001/4061* (2013.01)

(58) Field of Classification Search
None
See application file for complete search history.

(56) References Cited

U.S. PATENT DOCUMENTS

| | | | |
|---|---|---|---|
| 5,260,028 A | * 11/1993 | Astle | G01N 1/405 210/635 |
| 5,324,480 A | 6/1994 | Shumate | |
| 5,599,500 A | 2/1997 | Jones | |
| 5,760,299 A | 6/1998 | Johnson et al. | |
| 6,133,045 A | 10/2000 | Johnson et al. | |
| 6,240,984 B1 | 6/2001 | Fawcett et al. | |

(Continued)

OTHER PUBLICATIONS

UCTinc: "UCT Positive Pressure Manifold—Part 1", YouTube, Oct. 11, 2010 (Oct. 11, 2010), pp. 1-1, XP054977567, Retrieved from the Internet: URL:https://www.youtube.com/watch?v=HY8IXzSgVlk.

(Continued)

*Primary Examiner* — P. Kathryn Wright
(74) *Attorney, Agent, or Firm* — Dennis A. DeBoo; Audrey A. Millemann; Weintraub Tobin

(57) ABSTRACT

An automated positive pressure solid phase extraction apparatus and method comprising two tiered lifts devices each individually controllable to individually vertically translate within an elevator framework between a base on which the elevator framework is mounted and a manifold plate supported by the framework in a substantially horizontal plane parallel with and vertically above the two tiered lifts devices and a rectilinearly translating shuttle assembly comprising a shuttle supporting labware for rectilinear travel into and out of the elevator framework to handoff the labware to one of the two tiered elevator lifts or both.

2 Claims, 46 Drawing Sheets

(56) References Cited

U.S. PATENT DOCUMENTS 6,899,848 B1    5/2005  Chen et al.

OTHER PUBLICATIONS

BiotageLLC: "Biotage PRESSURE+ 96 Manifold demonstration", YouTube, Jun. 29, 2011 (Jun. 29, 2011), pp. 1-1, XP054977568, Retrieved from the Internet: URL:https://www.youtube.com/watch?v=_y-Zx_4MZNw&t=78s.
James Leontis: "ALD-III JANUS SPE 96 ASMS 2012.wmv", YouTube, Nov. 15, 2013 (Nov. 15, 2013), pp. 1-1, XP054977569, Retrieved from the Internet: URL:https://www.youtube.com/watch?v=rmJID7N0GPI.
ZinsserAnalytic: "Automated SPE (Solid Phase Extraction)—Expanded Edition", YouTube, May 28, 2013 (May, 28, 2013), pp. 1-1, XP054977571, Retrieved from the Internet URL:https://www.youtube.com/watch?v=U9qjE_0VT1k&t=106s.

* cited by examiner

At the start of this method, all axis of Automated Pipetting Workstation and Positive Pressure SPE Apparatus are initialized via software.

Software controls the Automated Pipetting Workstation to place a filter plate onto the Positive Pressure SPE Apparatus. Software then controls the Workstation to dispense a Conditioning Liquid into the filter plate. The Positive Pressure SPE apparatus moves the filter plate to the manifold via software control and applies user specified pressure for a user specified time period via software control.

Software controls the shuttle with the filter plate mounted thereon back to the Pipette Accessible Position where a Sample is dispensed into the filter plate by the Workstation via software control. The Positive Pressure SPE Apparatus is then controlled to move the filter plate back below the manifold where software controlled user specified pressure is applied for a user specified time period.

Software controls the shuttle with the filter plate mounted thereon back to the Pipette Accessible Position where a Washing Agent is dispensed into the filter plate by the Workstation via software control. The Positive Pressure SPE Apparatus is then controlled to move the filter plate back below the manifold where software controlled user specified pressure is applied for a user specified time period.

Filter plate remains engaged with the manifold and the Positive Pressure SPE Apparatus is software controlled to move the shuttle to the Pipette Accessible Position to receive a collection plate. The collection plate is moved under the filter plate and the filter plate is moved down on top of the collection plate. Then, both plates are moved out to the Pipette Accessible Position. All motions are software controlled. The Workstation then dispenses the elution agent into the filter plate via software control. Both plates are moved to engage the manifold where software controlled user specified pressure is applied for a user specified time period to push the sample of interest into the collection plate via software control.

To finalize this SPE process, the collection plate is moved to the Pipette Accessible Position for removal by the Workstation via software control. The filter plate is then moved to the Pipette Accessible Position for removal by the Workstation. The Positive Pressure SPE Apparatus is now ready to start the SPE process from the beginning.

FIG. 13

At the start of the Evaporation Process, software controls the automated pipetting workstation to place the evaporator adapter onto shuttle.

Next, the positive pressure solid phase extraction apparatus moves the evaporator adapter to the manifold via software control.

The positive pressure solid phase extraction apparatus is then software commanded to move the shuttle to the pipette accessible location via software control to receive a collection plate.

Under software control, the positive pressure SPE apparatus then moves the collection plate back to the lower elevator which is then software controlled to lift the collection plate to engage the needles of the evaporator adapter just above the liquid height in the collection plate. Then, user specified heated air is applied to the liquid surface for a use specified time period to evaporate the liquid and leaving behind the solute. Evaporation fumes are directed through a plenum to a port that is adapted to the user fume management system.

The positive pressure SPE apparatus then moves the shuttle with the collection plate back to the pipette accessible location via software control for presenting the collection plate back to the automated pipetting workstation accessible position for removal of the collection plate from the shuttle by the pipette workstation via software control.

The positive pressure SPE then moves the shuttle back to receive the evaporator adapter and move the evaporator adapter back to the pipette accessible location via software control for removal by the pipette workstation via software control.

AUTOMATED POSITIVE PRESSURE SOLID PHASE EXTRACTION APPARATUS AND METHOD

CROSS-REFERENCE TO RELATED APPLICATIONS

This application claims priority under 35 USC Section 119(e) to U.S. Provisional Patent Application No. 61/928,873, filed Jan. 17, 2014, the entire disclosure of which is incorporated herein by reference.

FIELD OF THE INVENTION

This invention relates generally to a positive pressure solid phase extraction apparatus and method and, in particular, to an automated positive pressure solid phase extraction apparatus and method having stand-alone utilization and utilization with, for example, an automated material handling system such as an automated pipetting workstation.

BACKGROUND OF THE INVENTION

Currently, the separation of compounds in a solid phase extraction (SPE) process is accomplished by vacuum and positive pressure methodologies. While automated systems exist for use with vacuum, the weakness is in that the application of vacuum is across the whole filter plate. This is because as media is pulled through a filter, the resulting compound/component cannot come into contact with anything except the well that is intended to catch the compound to eliminate potential cross contamination. For a filter plate that contains an array of wells (currently up to 384) the vacuum applied to an individual well in the array is not equal to any other well due to the resistance differences of the wells in the array as the media is filtered. Some wells in the array will pass the media through the filter faster than others and when they have completely passed the media, those wells become even less restrictive and thus allow more air to flow through subsequently reducing the amount of air flowing through the remaining wells. As a result, it is difficult to guarantee all wells have filtered their media within a given time allotment.

An additional weakness of currently known vacuum based devices is that user interaction is required in the selection and/or adjustment of adapters to set the height between the filter plate and the collection or micro plate for the purpose of engaging the nozzles of the filter plate into the wells of the collection or micro plate. The engagement is necessary to prevent possibility of cross contamination across wells. This manual process can be iterative requiring time and can be further problematic in determining the correct engagement to prevent cross contamination.

Examples of these vacuum based SPE devices are the AVS on the ML4000 and ML STAR, the CVS on the ML STAR, and the NVS on the ML Nimbus. All of these instrumentalities and systems are manufactured and sold by the assignee of the present patent application, Hamilton Company, 4970 Energy Way, Reno, Nev. 89502, United States Of America.

Positive Pressure is a solution to the problem of even flow distribution as flow restrictors can be employed to guarantee even distribution of pressure and flow to individual wells. Flow restrictors per well cannot be employed on a vacuum system as they would come into contact with the liquids being processed creating the potential for contamination. While there are positive pressure apparatus currently available, the weakness of those devices is that they are not, inter alia, friendly to automated pipetting workstations and require user interaction at virtually every stage of the SPE process as a stand-alone unit.

Hence, there is a need to overcome the significant shortcomings of the known prior-art as delineated hereinabove.

BRIEF SUMMARY OF THE INVENTION

Accordingly, and in one aspect, an embodiment of the invention ameliorates or overcomes one or more of the shortcomings of the known prior art by providing a positive pressure solid phase extraction (SPE) apparatus comprising a shuttle assembly having a shuttle reciprocally movable along a longitudinal length of a base plate on which the shuttle assembly is mounted; a tiered elevator lift assembly disposed on the base plate and vertically extending therefrom so as to partition the longitudinal length of the base plate into an accessible home position (e.g., a gripper and pipetter/probe head assembly accessible home position) and an inaccessible away position under a vertically elevated manifold plate for presenting labware from the shuttle to an upper and/or lower tiered lift device of the tiered elevator assembly located below the manifold plate wherein the upper and lower tiered lift devices and the shuttle are individually controllable to shuttle labware into the elevator assembly and present it to the upper and lower lifts of the tiered elevator lift mechanism having vertically controllable lift heights of one labware piece or two tiered labware pieces up to a manifold plate positioned vertically above the upper and lower tiered lift devices so as to allow controlled settings of the height between two tiered labware pieces being presented to the manifold plate such that in one aspect cross contamination is precluded such as is exemplified when the tiered labware being presented to the manifold is a filter plate surmounting a collection at the controlled height therebetween.

In another aspect, an embodiment of the invention provides an automated positive pressure SPE apparatus that is presented to an accessible location on an automated pipetting workstation. The automated pipetting workstation interacts with the automated positive pressure SPE apparatus by placing labware on and removing labware from a shuttle of a shuttle assembly of the apparatus that is reciprocally movable along a longitudinal length of a base plate on which the shuttle assembly is mounted. Additionally, the pipetting workstation dispenses liquids to the labware as needed during the SPE process. Furthermore, the positive pressure SPE apparatus comprises a tiered elevator lift assembly mounted on the base plate and vertically extending therefrom such that the longitudinal length of travel of the shuttle along the base plate allows the shuttle to reciprocate in and out of the tiered elevator lift assembly for presenting labware to an upper tiered lift device and a lower tiered lift device of the tiered elevator lift assembly such that, after the interaction with the automated pipetting workstation, the apparatus shuttles the labware into the tiered elevator lift assembly and presents the labware to the upper and lower tiered lift devices that are independently driven to present the labware such as a filter plate to a positive pressure manifold disposed in a horizontal plane vertically above and substantially parallel to the upper and lower tiered lift devices wherein a user specified and software controlled pressure is applied to the filter plate via the positive pressure manifold for a user specified and software controlled time period for the purpose of separating liquid compounds into their individual components of interest. The tiered elevator lift assembly can further provide simultaneous or sequential vertical lifting of a collection or waste plate below the filter plate. Additionally, and in one aspect, the tiered elevator lift assembly is software controlled to provide positioning of the filter plate and collection plate to engage the nozzles of the filter plate into the wells of the collection plate via software labware definitions eliminating the need for user interaction for adjustment. This further allows for multiple combinations of filter and collection plates to be used without user interaction for adjustment.

In another aspect, an embodiment of the invention provides an automated positive pressure SPE apparatus comprising a process security system for providing process security by use of pressure and temperature sensors that monitor the pressure and temperature change over time for an array of wells, for example up to 96, during the SPE process. The use of the pressure sensors provides process security for each well of the labware by collecting pressure data which the process security system utilizes to construct a curve of the process. This curve is then compared by the process security system to a previously stored standard acceptable curve with tolerance boundaries defined from which a pass/error decision is made by the process security system regarding the completeness and timeliness of the process being measured. Errors are presented to the user and recorded permanently in a log file with time and date for traceability. The temperature sensors provide additional process security in applications that are sensitive to temperature variances by recording the temperature of each well in the labware at various times during the process and having, for example, a bench mark to which the recorded temperatures are compared to for making pass/error decision. Temperature values are also recorded permanently in a log file with date and time for traceability and future use.

In another aspect, an embodiment of the invention provides an automated positive pressure SPE apparatus that serves as an evaporator for downstream SPE processes by placing an evaporator adapter onto the shuttle assembly which presents the adapter to the upper tiered lift device. The upper tiered lift device presents the evaporator adapter to the manifold plate through which the apparatus controls both the flow and heat added via a heater control unit to the system air. Subsequently, this air flows through the evaporator adapter into labware which is presented to the adapter by the lower tiered lift device. The labware is presented in close proximity to the evaporator adapter such that the controlled heated air is directed onto the liquid surface to be evaporated without the adapter being in direct contact with the liquid being evaporated. Evaporated vapors are directed through a plenum to a duct which is connected to the user's ventilation system. During the evaporation process, the lower tiered lift device moves to keep the liquid being evaporated in close proximity to the evaporator adapter to maximize efficiency of the evaporation process.

In another aspect, an embodiment of the invention provides an automated positive pressure SPE apparatus that serves as a tip dryer by means of presenting a rack of tips to the upper tiered lift device by the shuttle assembly. The upper tiered lift device presents the rack of tips to the manifold plate through which the apparatus controls the flow of controlled heated air. Subsequently, this air flows through the individual tips and any liquid is captured by the shuttle assembly and directed to a liquid waste container.

In another aspect, an embodiment of the invention provides an automated positive pressure SPE apparatus that serves as a cap mat sealing device. First, labware is placed on the shuttle assembly. Then a cap mat is placed onto the top of the labware. The shuttle assembly presents the stack to the upper tiered lift device. The upper tiered lift device presents the stack to the manifold plate and applies force as if attempting to seal the labware against the manifold plate in the SPE process. This will seat the cap mat into the labware. Air pressure can be additionally applied to further seat the cap mat into the labware to create the necessary seal.

Further advantages of the automated positive pressure SPE apparatus and method will become apparent from the detailed description provided below, when taken together with the attached drawings and claims. It should be understood, however, that numerous modifications and adaptations may be resorted to without departing from the scope and fair meaning of the claims as set forth hereinbelow following the detailed description of the invention.

BRIEF DESCRIPTION OF THE DRAWINGS

FIG. 13 is a further detailed flow diagram of the automated positive pressure SPE sequencing process of the automated positive pressure SPE apparatus charted in FIG. 12.

FIG. 34 is a further detailed flow diagram of the evaporation process.

DETAILED DESCRIPTION OF THE INVENTION

Figure 1:
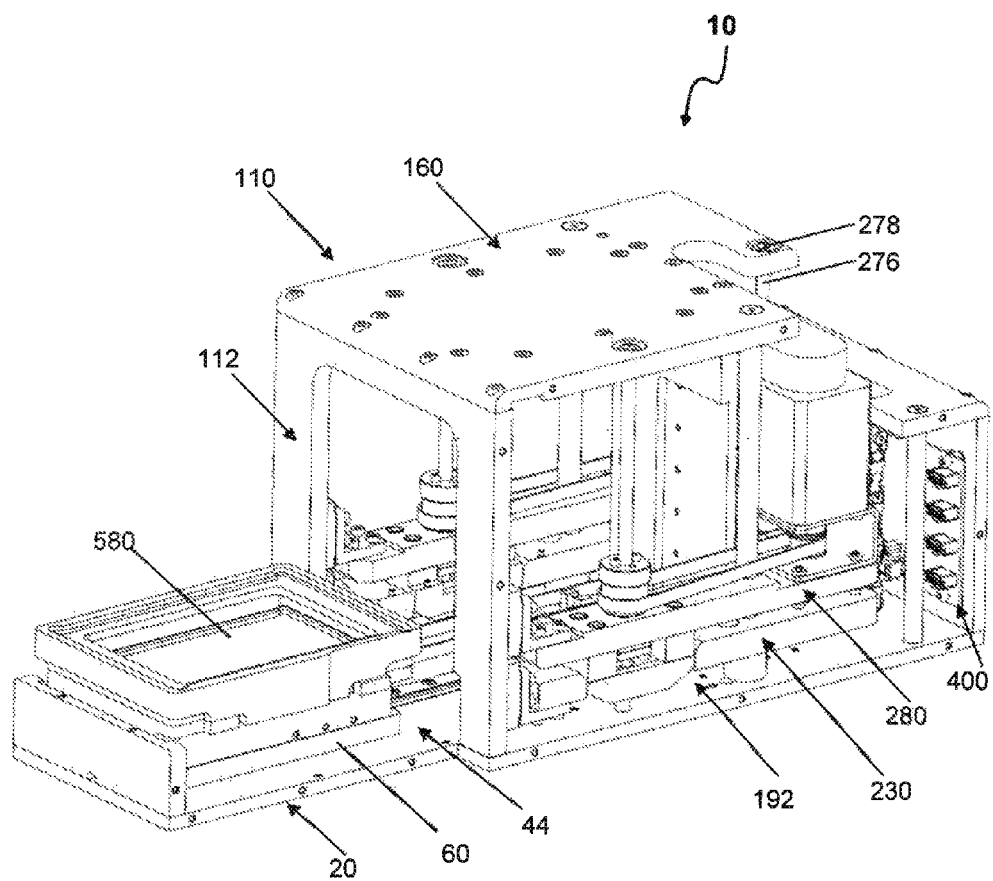
FIG. 1 is a forward lateral end and front longitudinal side perspective view of an embodiment of an automated positive pressure solid phase extraction (SPE) apparatus with lateral side plates removed therefrom.

Considering the drawings, wherein like reference numerals denote like parts throughout the various drawing figures, reference numeral 10 is directed to an embodiment of an automated positive pressure solid phase extraction (SPE) apparatus and reference 410 (FIG. 3) is directed to a positive pressure solid phase extraction system formed by the positive pressure solid phase extraction apparatus 10 and associated method described below in combination with an automated material handling system in the form of, but not limited to an automated pipetting workstation 420.

Referring to FIG. 1, and in its essence, apparatus 10 comprises a base plate 20; a shuttle assembly 44 comprising a shuttle 60; an elevated manifold assembly 110 comprising a manifold framework assembly 112 and a manifold plate assembly 160; a waste tray assembly comprising a waste tray 580; and a tiered elevator lift assembly 192 comprising a lower tiered lift device 230 and an upper tiered lift device 280.

Figure 2:
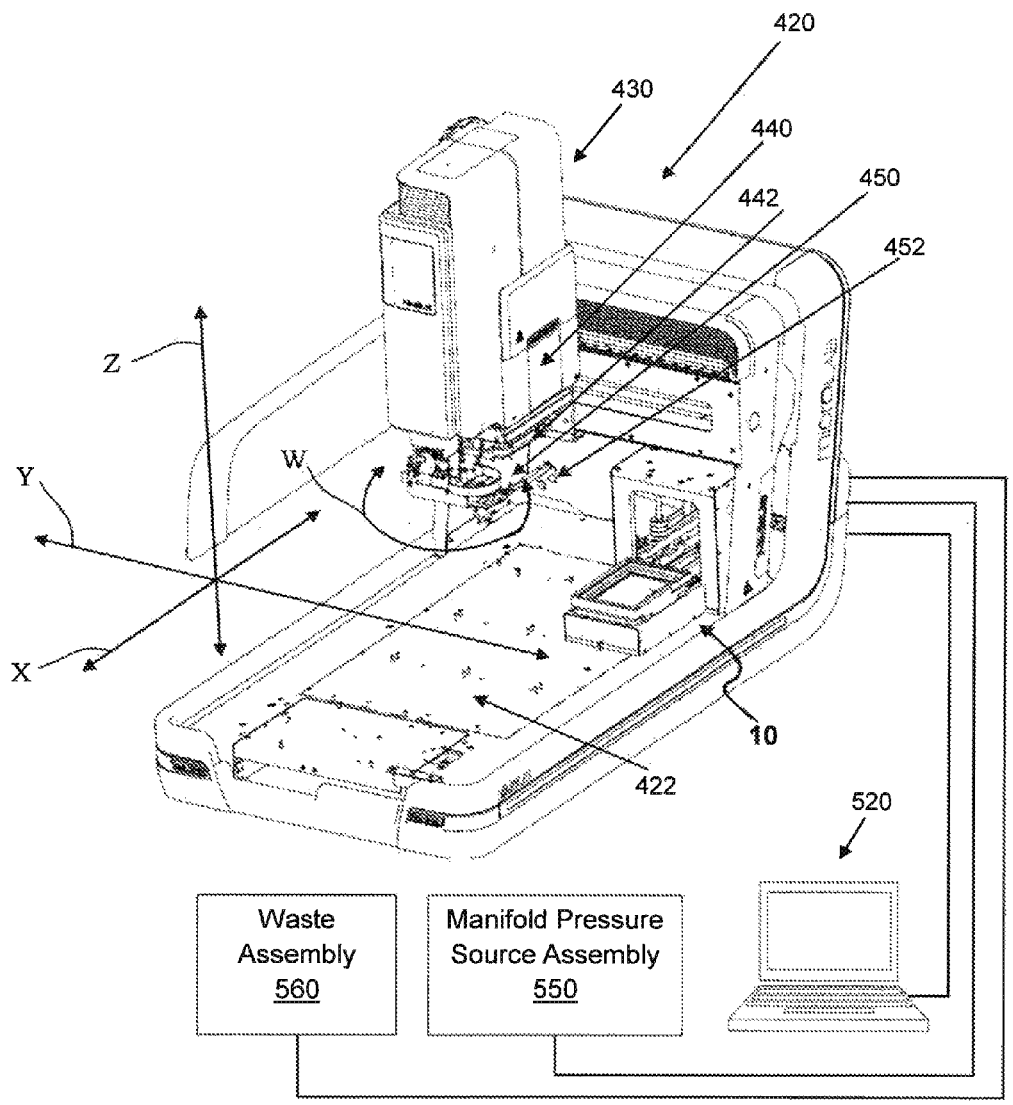
FIG. 2 is a perspective view illustrating the automated positive pressure SPE apparatus disposed on a rear lateral deck portion of an embodiment of an automated pipetting workstation, the workstation having a gripper and pipetter/probe head assembly operatively coupled to a robotic gantry and the view further illustrating a computer operatively coupled to the workstation and the automated positive pressure SPE apparatus, and the view further illustrating a manifold pressure source assembly and a waste assembly operatively coupled to the automated positive pressure SPE apparatus.
Figure 32:
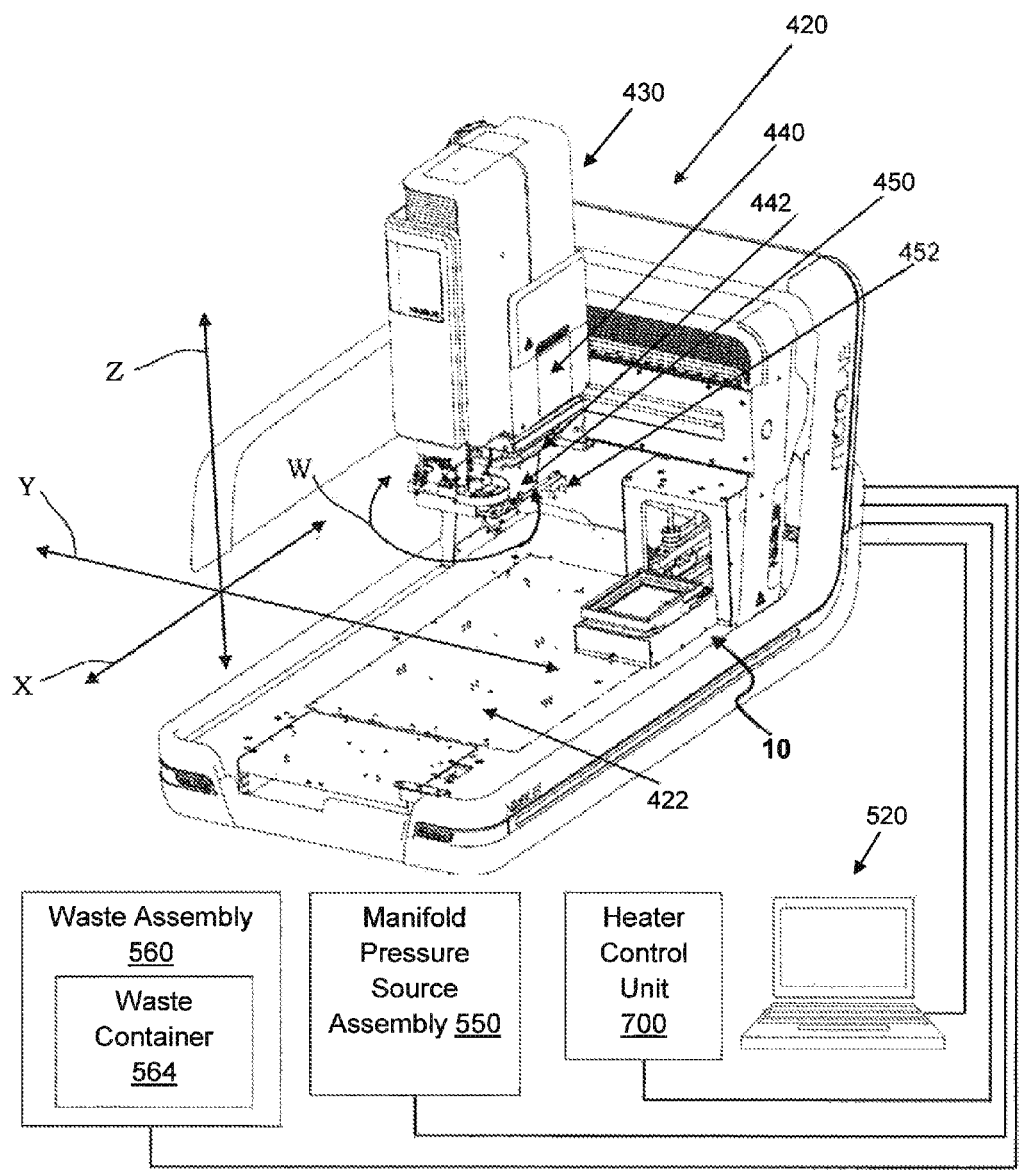
FIG. 32 is a perspective view illustrating the automated positive pressure SPE apparatus disposed on an automated pipetting workstation, the workstation having a gripper and pipetter/probe head assembly operatively coupled to a robotic gantry and the view further illustrating a computer operatively coupled to the workstation and the automated positive pressure SPE apparatus, and the view further illustrating a heater control unit, the manifold pressure source assembly, and the waste assembly operatively coupled to the automated positive pressure SPE apparatus.

FIG. 2 illustrates an embodiment of the positive pressure SPE apparatus 10 disposed on a posterior portion of a deck 422 of the automated pipetting workstation 420. As also illustrated, the positive pressure SPE apparatus 10 is operatively coupled to a waste assembly 560, a manifold pressure source assembly 550, and a computer 520 that is also operatively coupled to workstation 420. As illustrated in FIG. 32, the positive pressure SPE apparatus 10 is further operatively coupled to a heater control unit 700.

Workstation

Referring to FIG. 2, and in one embodiment, the automated pipetting workstation 420 comprises a robotic gantry 430 operatively carrying, vertically above workstation deck 422, both a multi-channel pipetting assembly 440 having a multi-channel pipetting head 442 and a labware gripper arm assembly 450 having engaging fingers 452.

Robotic gantry 430 provides three degrees of freedom that include longitudinal translation along the direction of the double ended arrow "X", latitudinal translation along the double ended arrow "Y" and vertical translation along the double ended arrow "Z" so that the pipetting head 442 and the engaging fingers 452 can move along the length and width of the deck 422 and vertically up and down relative thereto. Additionally, the labware gripper atm assembly 450 provides the engaging fingers 452 with the ability to rotate about the double ended arrow "W" and to provide telescopic extension. The engaging fingers 452 grasp side edges of labware to be described.

In general, and as conventional in the art and informed by the instant disclosure, a fluid delivery system provides a controlled delivery of fluid within the multi-channel pipetting head 442 comprising a multiplicity of individual probe tips each of which can carry same or different fluids as dictated by the system setup. In one embodiment, the multi-channel pipetting head 442 comprises 96 tips oriented in an 8×12 array. Other probe arrays and tip populations are possible.

In one embodiment, the control of the multi-channel pipetting head 442 is controlled by the computer 520 which can also control the robotic gantry 430 and the positive pressure SPE apparatus 10 and its sequencing protocols.

Controller

Figure 3:
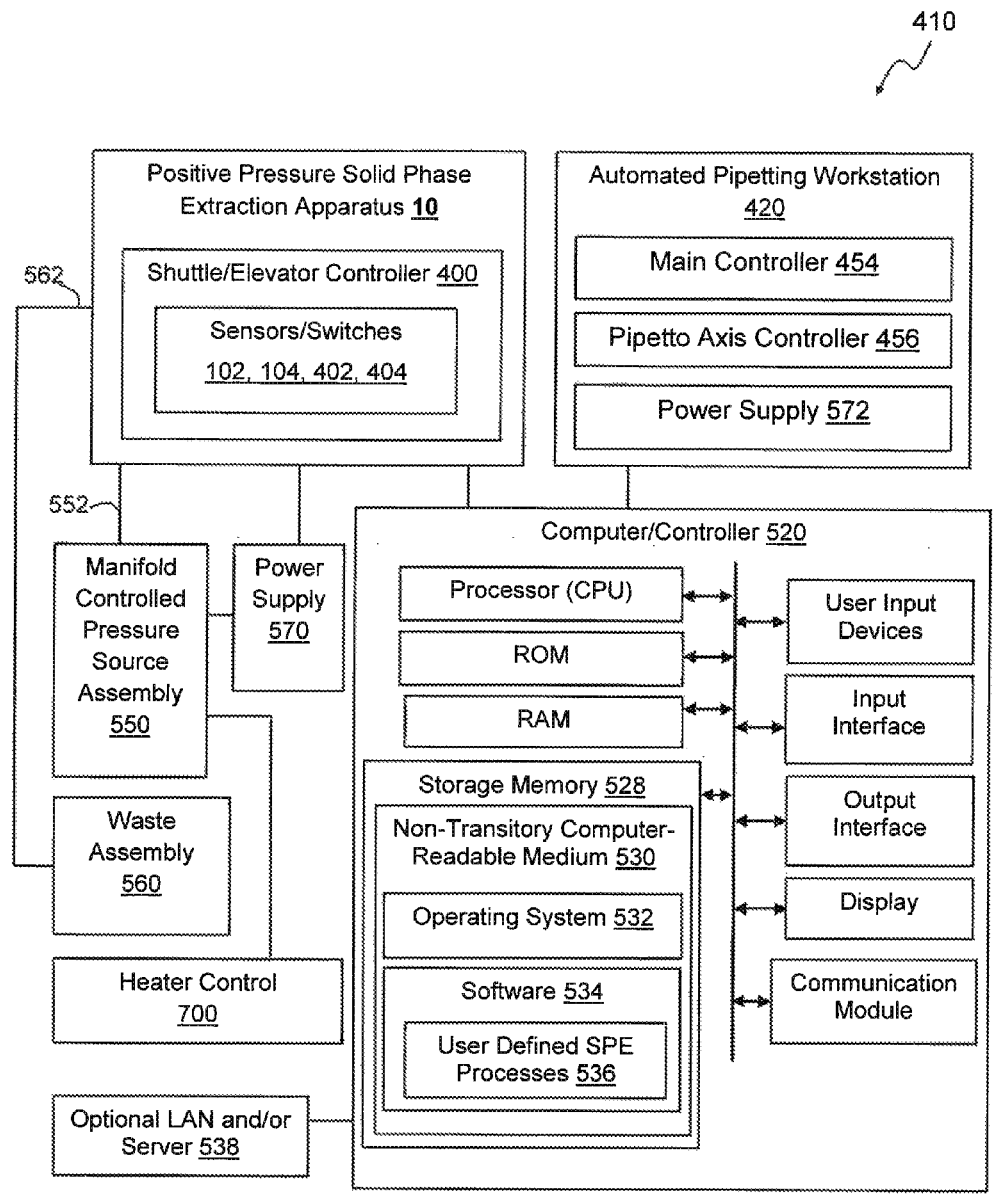
FIG. 3 is a general block diagram view of the automated positive pressure SPE apparatus shown operatively coupled to the automated pipetting workstation, both of which are operatively coupled to a computer/controller that can be connected to an optional LAN or server.
Figure 7:
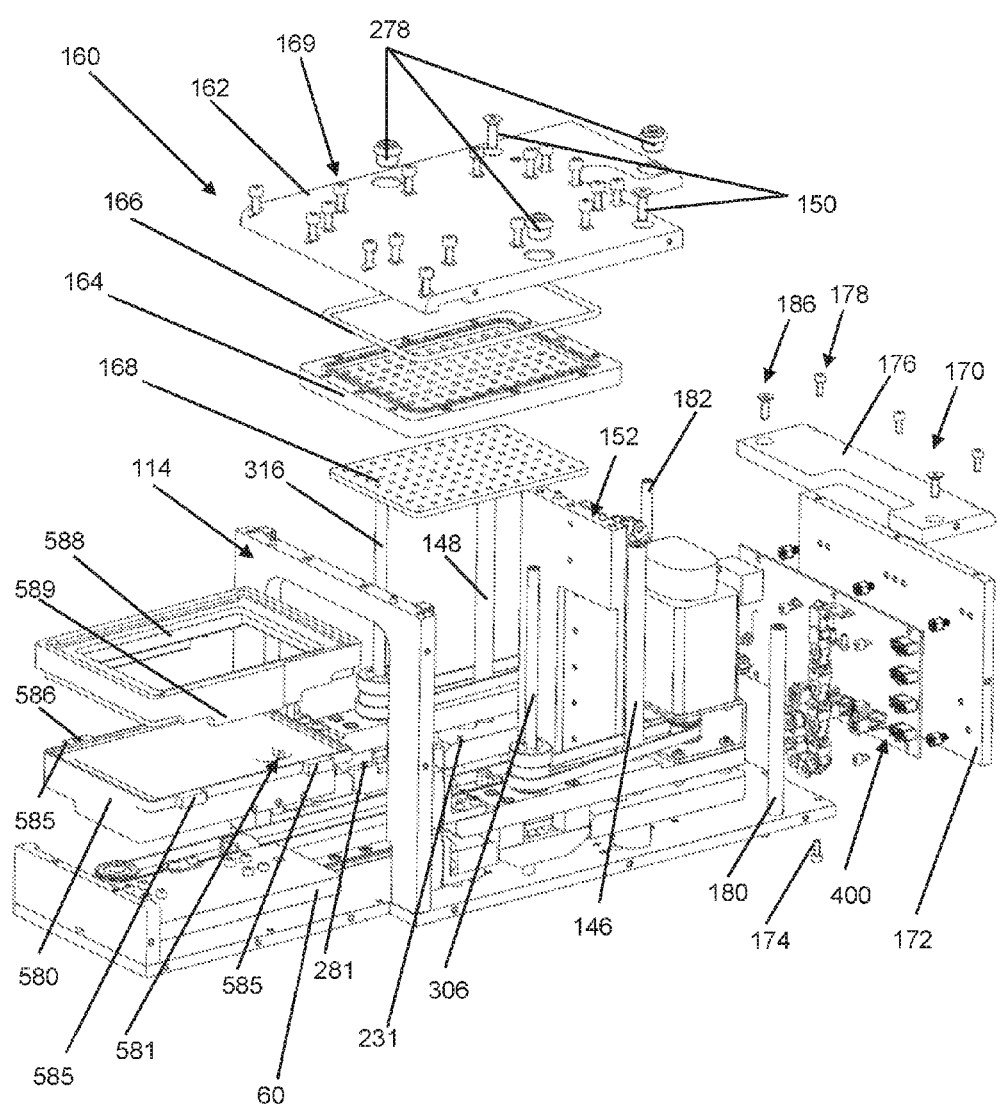
FIG. 7 is a partial exploded parts perspective view detailing an elevated manifold assembly and PCB housing and PCB controller and a perspective view of the shuttle assembly, and a tiered elevator lift assembly of the automated positive pressure SPE apparatus.

Referring now to FIGS. 1 through 3, and in one embodiment, the positive pressure SPE apparatus 10 comprises a controller 400 laid out on a printed circuit board (PCB) thereby defining a controller PCB 400 that attaches to a rear or posterior latitudinal plate 172 via standoffs and screws as further illustrated in FIG. 7.

The controller 400 is operatively coupled to both the automated pipetting workstation 420 and computer/controller 520 for providing communication therewith for controlling the tiered elevator lift assembly 192 and the shuttle assembly 44.

Additionally, and in one embodiment, the controller 400 is operatively coupled to four sensors such as optical interrupt switches 102, 104; 402, and 404.

Figure 4:
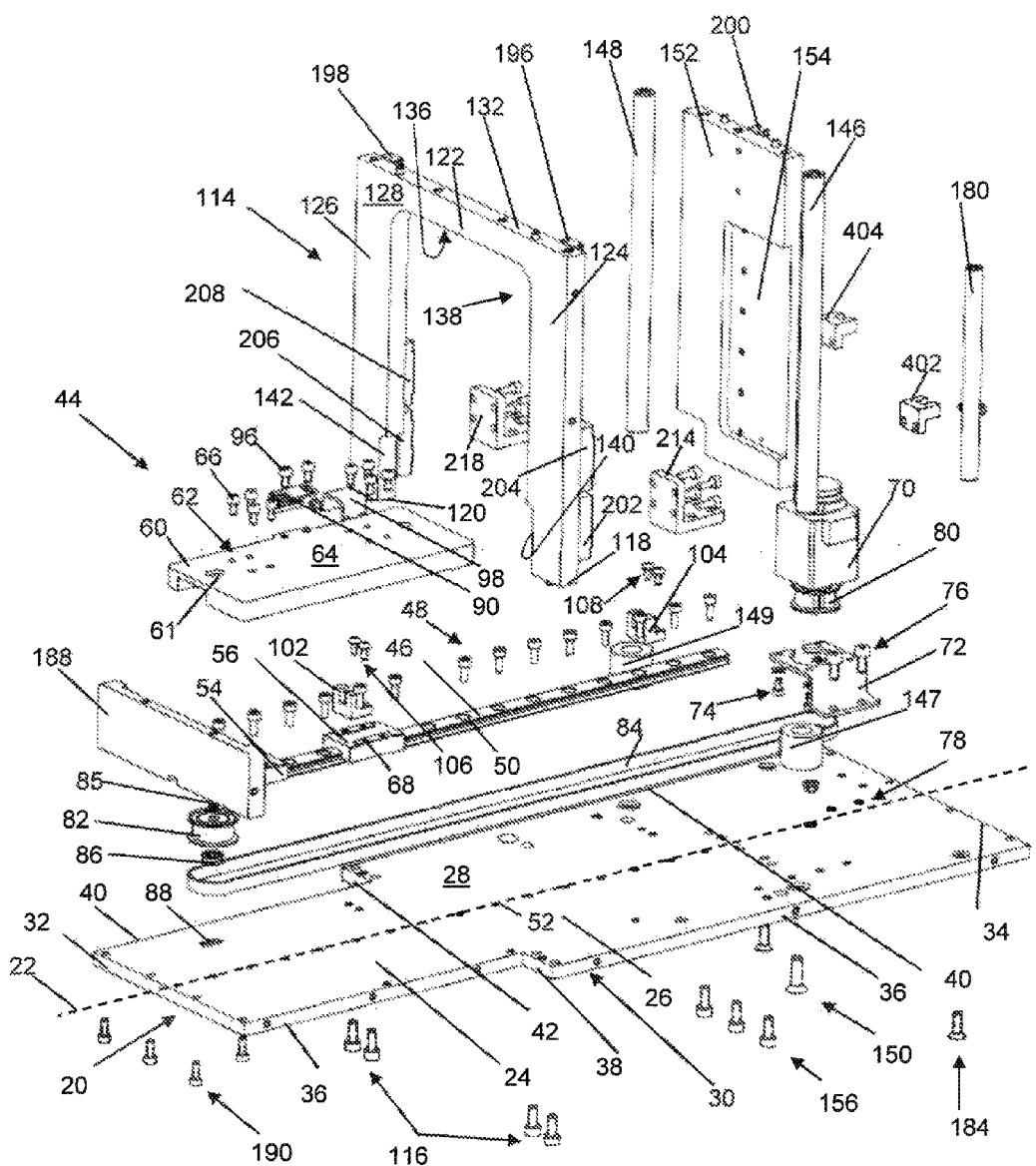
FIG. 4 is an exploded parts perspective view detailing a base plate, a shuttle assembly, a manifold framework assembly, and a vertical guide rail assembly of the automated positive pressure SPE apparatus.

Referring to FIGS. 3 and 4, and in one embodiment, sensors 102, 104 provide an indication of one of two positions or states of the shuttle 60 having corresponding sensor target, trip, or flag member 98 mounted on the side of the shuttle 60 as delineated below. Sensor 402 provides an indication of a defined lower home position of the lower lift device 230 having corresponding sensor target, trip, or flag member 406 (FIG. 5) mounted on and interiorly downwardly depending from support member 234 of forked lower lift member 232. Similarly, sensor 404 provides an indication of a defined lower home position of the upper lift device 280 having corresponding sensor target, trip, or flag member 408 (FIG. 10) mounted on and interiorly downwardly depending from support member 286 (FIG. 8) of forked upper lift member 282. The controller 400 can communicate sensor information to the computer/controller 520 and workstation 420.

Furthermore, power supply 570 provides power to the positive pressure SPE apparatus 10 and to controller 400. The automated pipetting workstation 420 receives power from power supply 572.

As noted above, the computer/controller 520 can also provide control of the automated pipetting workstation 420 via a main controller 454 and Pipetto axis controller 456. As was also noted above, the computer/controller 520 can also provide control of the manifold controlled pressure source assembly 550 and waste assembly 560. The computer/controller 520 can also provide control of the heater control unit 700.

Moreover, computer/controller 520 comprises storage memory 528 which comprises a non-transitory computer readable medium 530 having an operating system 532 and software 534 stored thereby. User defined SPE processes 536 for the positive pressure solid phase extraction apparatus 10 may also be stored in the nontransitory computer readable medium 530. Computer/controller 520 may be operatively couple to optional LAN and/or server 538.

Base Plate

Now referring to FIG. 4, and in one embodiment, the apparatus 10 comprises base plate 20 having a central longitudinal axis 22 that is also the central longitudinal axis of the apparatus 10. The base plate 20 comprises forward and rearward rectangular sections 24 and 26 with the rearward rectangular sections 26 being of greater length and width than the forward rectangular section 24, but of equal height defining a uniform cross sectional area of the base plate 20 that extends between an upper planar surface 28 and a lower planar surface 30.

Base plate 20 further comprises a forward or anterior end 32 and a rearward or posterior end 34. A first or front longitudinal side 36 of the base 20 extends between the anterior and posterior ends 32 and 34 with a step 38 at the transition edge between the rearward and forward rectangular sections 24 and 26. Similarly, a second or rear longitudinal side 40 extends between the anterior and posterior ends 32 and 34 with a step 42 at the transition edge between the two rectangular sections 24, 26.

Shuttle Assembly

Figure 5:
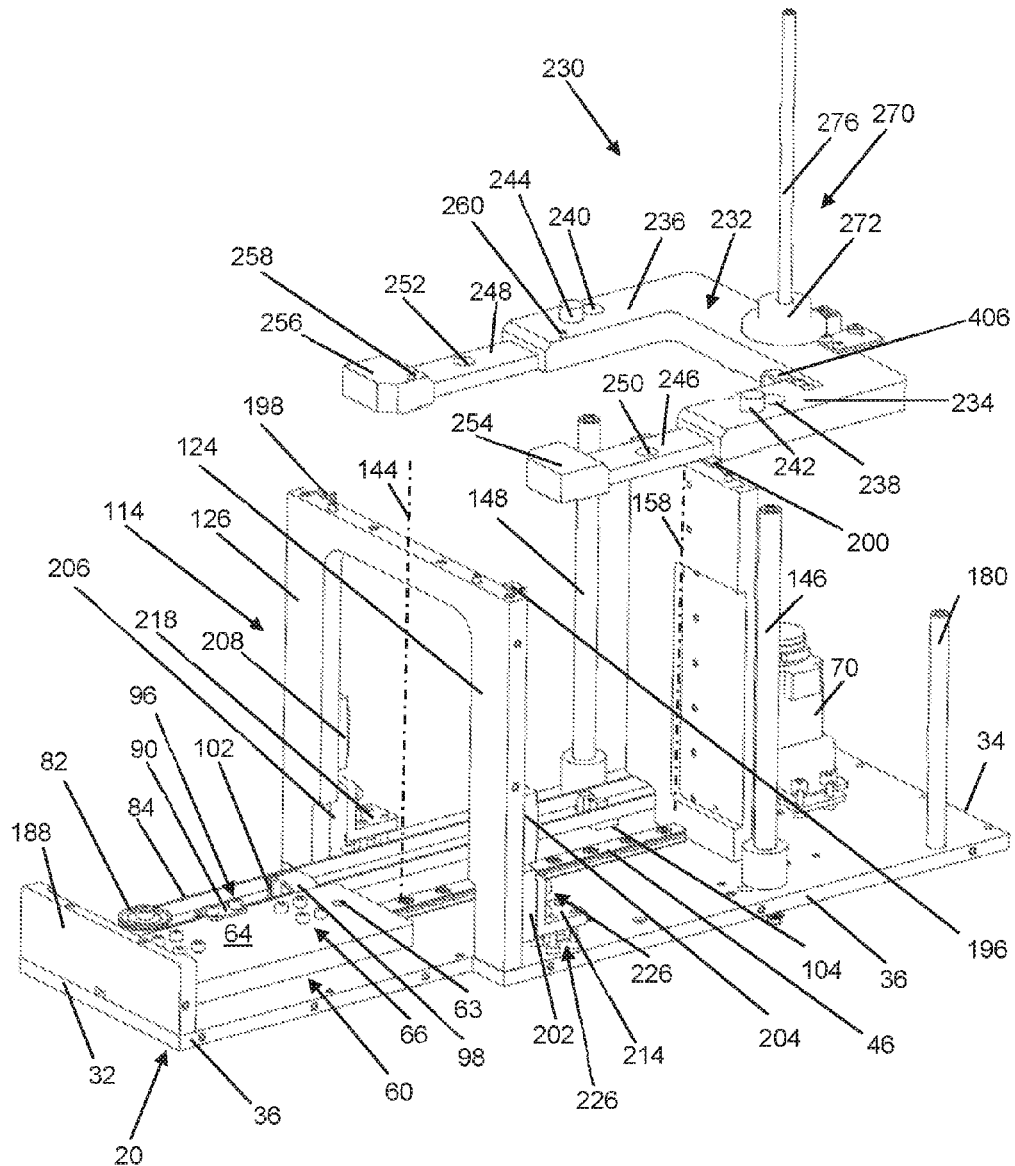
FIG. 5 is a partial exploded parts perspective view detailing parts of the shuttle assembly and a lower tiered lift device.

Referring to FIGS. 4 and 5, shuttle assembly 44 comprises a linear guide rail 46 having a predetermined length attached on the upper planar surface 28 of the base plate 20 along the central longitudinal axis 22 thereof utilizing bolts 48 passing through guide rail holes 50 and threading into guide rail base holes 52.

Additionally, the shuttle assembly 44 comprises a pair of shuttle bearing guides 54 and 56 that are slideably mounted on linear guide rail 46 along its predetermined length.

The shuttle assembly 44 further comprises a shuttle 60 slideably mounted on linear guide rail 46 along its predetermined length via shuttle bearing guides 54, 56. Specifically, the shuttle 60 comprises two longitudinally spaced apart pairs of four holes 62 disposed through an upper surface 64 of the shuttle at a fore and aft location thereof. In turn, two pair of four bolts 66 respectively pass through the two pair of four holes 62 and thread into complementary spaced threaded bores 68 disposed through the upper surface of each shuttle bearing guide 54, 56 thereby slideably mounting the shuttle and any mounted labware onto the linear guide rail 46 so that the shuttle is reciprocally movable along the predetermined length of the linear guide rail 46. Shuttle 60 comprises a set of fore and aft locating apertures 61 (FIG. 4) and 63 (FIG. 5) for receipt of complementarily spaced labware locating pins.

Furthermore, the shuttle assembly 44 comprises motor 70 mounted on base plate 20 proximate a posterior longitudinal corner of base plate 20 via a generally inverted L-shaped bracket 72 having a horizontal landing attaching to motor 70 via motor bolts 74 and to the base plate 20 via bolts 76 threading into bores 78 of base plate 20 such that the motor is vertically spaced from the base plate 20 for defining a pulley space. Two pulleys 80 and 82, over which a timing belt 84 runs, are arranged longitudinally spaced apart by a predetermined distance and such that the timing belt 84 runs parallel with and between the linear guide rail 46 and the rear longitudinal side 40 of the base plate 20. In one embodiment, the length or span of the timing belt 84 along the base plate 20 is greater than the length of the linear guide rail 46. Pulley 80 is the driving pulley and is fitted within the pulley space under the L-shaped bracket 72 and is operatively coupled to the drive shaft of the bracket supported motor 70. The driven pulley 82 is rotateably supported by a shaft 85 and a disk-shaped member 86 which is fitted into a pulley attachment hole 88 disposed in base plate 20. The pair of pulleys 80, 82, and timing belt 84 combine to function as drive linkage translating rotary motion of the shaft of the motor 70 into linear motion of the shuttle 60 as further detailed below.

Figure 6:
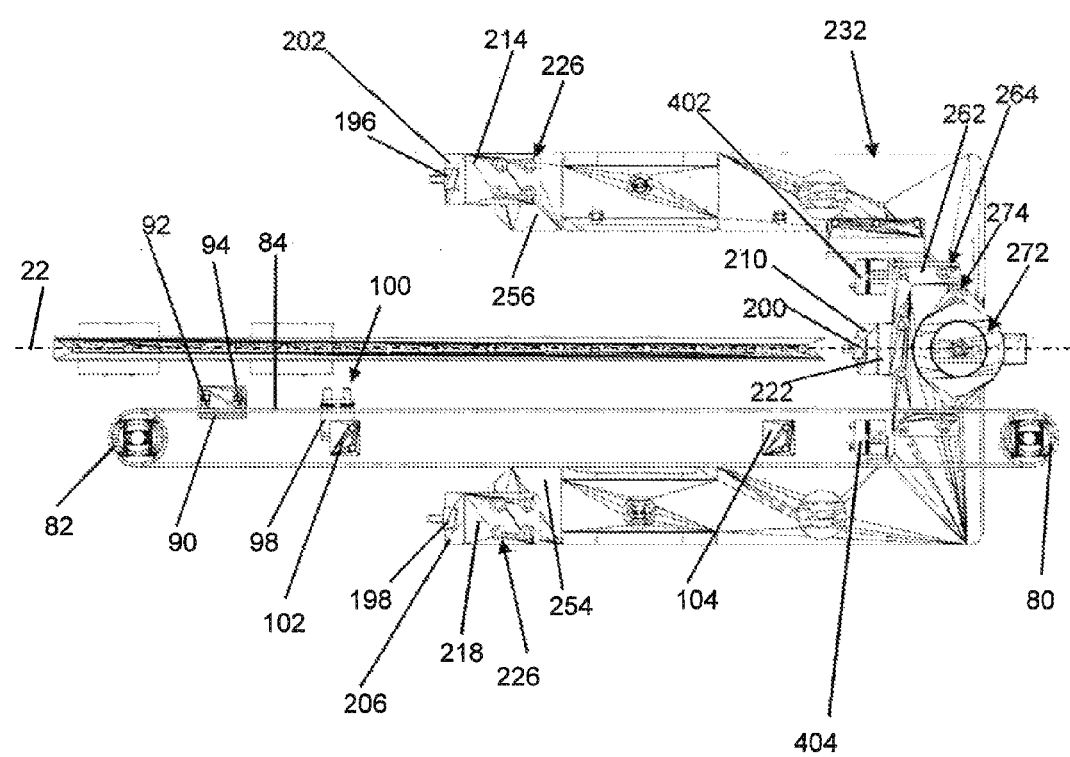
FIG. 6 is a bottom plan view detailing the shuttle assembly and the lower tiered lift device of the automated positive pressure SPE apparatus.

Moreover, and referring to FIGS. 5 and 6, the timing belt 84 is interposed between a bent bracket 90 and a pair of fixing blocks 92, 94 (FIG. 6). The bent bracket 90 is attached to the upper planar surface 64 of the shuttle 60 via bolts 96.

Thus, when the timing belt 84 runs over the driving and driven pulleys 80, 82 the rotation of the motor 70 is translated into linear motion of the shuttle 60 along the linear guide rail 46 in a direction away or toward a home position.

Referring to FIGS. 4 and 6, the shuttle assembly 44 further comprises the sensor target, trip, or flag member 98 attached to the rear longitudinal side of the shuttle 60 via bolts 100.

Additionally, the shuttle assembly 44 comprises the two aligned longitudinally spaced sensors 102 and 104 that are of an interrupt style that detect the presence of the flag member 98 passing adjacent or therethrough. The two aligned longitudinally spaced sensors 102 and 104 are secured to the base plate 20 via bolts 106 and 108 respectively.

Sensor 102 indicates when the shuttle 60 is in the predefined home position (a gripper and pipetter/probe head assembly accessible home) juxtaposed vertically above the forward rectangular section 24 of the base plate 20. Similarly, sensor 104 indicates when the shuttle 60 is in the predefined fully longitudinally extended position juxtaposed vertically above the rearward rectangular sections 26 of the base plate 20. The triggering or detection signals are transmitted to the controller 400 and computer 520 for use in control of the rectilinear movement of shuttle 60. In one embodiment, these are utilized with conventional internal motor encoding in locating shuttle 60 horizontally along linear guide rail 46.

Elevated Manifold Assembly

Referring back to FIG. 1, and as noted above, apparatus 10 further comprises an elevated manifold assembly 110 comprised of a manifold framework assembly 112 supporting a manifold plate assembly 160 in a substantially horizontal plane parallel to and vertically above the upper planar surface 28 of the base plate 20 at a predetermined distance.

Manifold Framework Assembly

Now referring to FIGS. 1 and 4, manifold framework assembly 112 comprises an inverted, generally U-shaped vertical support plate 114 vertically upwardly extending from the upper planar surface 28 of the base plate 20. In one embodiment, the U-shaped vertical support plate 114 is disposed at an anterior latitudinal edge of the second rectangular section 28 of base plate 20 immediately adjacent the first rectangular section 24 in a plane substantially perpendicular to the longitudinal axis 22 of the base plate 20. Bolts 116 extend through the lower planar surface 28 of the base plate 20 and threadedly couple with threaded blind bores disposed through horizontal planar ends 118, 120 of U-shaped vertical support plate 114 for fixedly attaching the support plate 114 to base plate 20.

Vertical support plate 114 has a substantially uniform U-shaped cross-sectional area and comprises a transverse member 122 having outer ends transitioning into a pair of generally parallel vertical main frame members 124, 126 terminating into the horizontal planar ends 118, 120.

The vertical support plate 114 further comprises a substantially planar vertical anterior or exterior surface 128 and a substantially planar vertical posterior or interior surface 130 (FIG. 9) spaced from the anterior surface 128. As illustrated in FIG. 4, the vertical support plate 114 comprises an outer periphery defined by a horizontally disposed upper exterior surface of the transverse member 122 and generally parallel vertical exterior side surfaces of respective main frame members 124, 126.

Additionally, the vertical support plate 114 comprises a generally U-shaped inner peripheral surface 136 defining a U-shaped opening 138. The U-shaped inner periphery or surface 136 comprises a horizontally disposed upper interior surface having opposing ends that arcuately transition downwardly into generally parallel vertical interior side surfaces of respective main frame members 124, 126 wherein the interior side surfaces transition into respective recessed surfaces 140, 142 defining interiorly notched lower ends of respective main frame members 124, 126.

Referring to FIGS. 4 and 5, the U-shaped opening 138 is centrally disposed through the vertical support plate 114 such that the central vertical axis of both are coincident and defined by a central vertical axis 144 of the vertical support plate 114. The central vertical axis 144 of the vertical support plate 114 is normal to and coplanar with the central longitudinal axis 22 of the base plate 20 and the linear guide rail 46 that is disposed along central longitudinal axis 22. Vertical main frame members 124, 126 are equally latitudinally spaced from the central vertical axis 144 of the vertical support plate 114 for allowing through passage of the shuttle 60 with or without supported lab ware to shuttle between the first predefined home position (the gripper and pipetter/probe head assembly accessible home) juxtaposed vertically above the forward rectangular section 24 of the base plate 20 and the second predefined fully longitudinally extended position juxtaposed vertically above the rearward rectangular sections 26 of the base plate 20.

Additionally, vertical manifold framework assembly 112 comprises two vertical support rods 146 and 148 longitudinally disposed a predetermined distance posterior to and in respective parallel relation with the vertical main frame members 124, 126 of the vertical support plate 114. Rods 146 and 148 are attached to the base plate and manifold plate assembly with bolts 150. Spacers 147, 149 circumscribe respective rods 146, 148 adjacent the upper surface 28 of base plate 20.

Furthermore, vertical manifold framework assembly 112 comprises a longitudinally rearward or back central vertical support plate 152. Back central vertical support plate 152 has a substantially rectangular shape with a substantially uniform cross section with the exception of an anterior recessed portion 154. In one embodiment, recessed portion 154 provides extra clearance for the shuttle 60 with or without supported labware. The faces and edges of the support plate 152 are substantially planar. The rearward central vertical support plate 152 vertically upwardly extends from the base plate 20 in a plane substantially perpendicular to the base plate 20. Bolts 156 extend through the lower planar surface 28 of the base plate 20 and threadedly couple with threaded blind bores disposed through horizontally inferior planar end of back central vertical support plate 152 for fixedly attaching the plate 152 to base plate 20.

Referring to FIG. 5, the back central vertical support plate 152 comprises a central vertical axis 158 that is normal to and coplanar with the central longitudinal axis 22 of the base plate 20 and the linear guide rail 46 that is disposed along central longitudinal axis 22. Accordingly, vertical axis 144 and vertical axis 156 are longitudinally aligned and spaced by a predefined longitudinal distance.

Manifold Plate Assembly

Referring to FIGS. 1 and 7, and as noted above, the elevated manifold assembly 110 comprises the manifold plate assembly 160 disposed in a substantially horizontal plane parallel to and vertically above the upper planar surface 28 of the base plate 20 at a predetermined distance.

As illustrated in the embodiment of FIG. 7, the manifold plate assembly 160 comprises a top plate 162 conventionally coupled to a manifold 164 via a manifold top plate gasket 166 sandwiched between the top plate 162 and manifold 164. The manifold plate assembly 160 further comprises an inferiorly disposed plate gasket 168 attached to an inferior or bottom surface of the manifold 164.

As illustrated, a multiplicity of bolts 169 are utilized to attach the manifold to the superior horizontal planar surface of the vertical support plate 114 and the back central vertical support plate 152 and to further attach to rods 146 and 148. Additionally, a plurality of bolts 169 are utilized to attach manifold 164 to top plate 162 with the manifold top plate gasket 166 interposed therebetween and with the manifold 164 carrying the inferiorly disposed plate gasket 168.

The manifold controlled pressure source assembly includes a pressure line 552 (FIG. 3) operatively coupling to the manifold in a conventional manner via elbow fitting 554 (FIG. 14) disposed through top plate 162 of the manifold plate assembly 160.

PCB Housing and Forward End Cap

Positive pressure SPE apparatus 10 further comprises a PCB housing 170 comprising the posterior latitudinal plate 172 vertically extending from and attached to a reward lateral upper planar edge of base plate 20 via bolts 174 and a horizontal plate 176 attached to the latitudinal plate 172 via bolts 178. The housing 170 further comprises a pair of latitudinally spaced apart and longitudinally offset rods 180, 182 that are attached to base plate 20 via bots 184 (FIG. 4) and to horizontal plate 176 via bolts 186.

Positive pressure SPE apparatus 10 further comprises end cap 188 vertically extending from and attached to a forward lateral upper planar edge of base plate 20 via bolts 190.

Waste Tray Assembly

Figure 9:
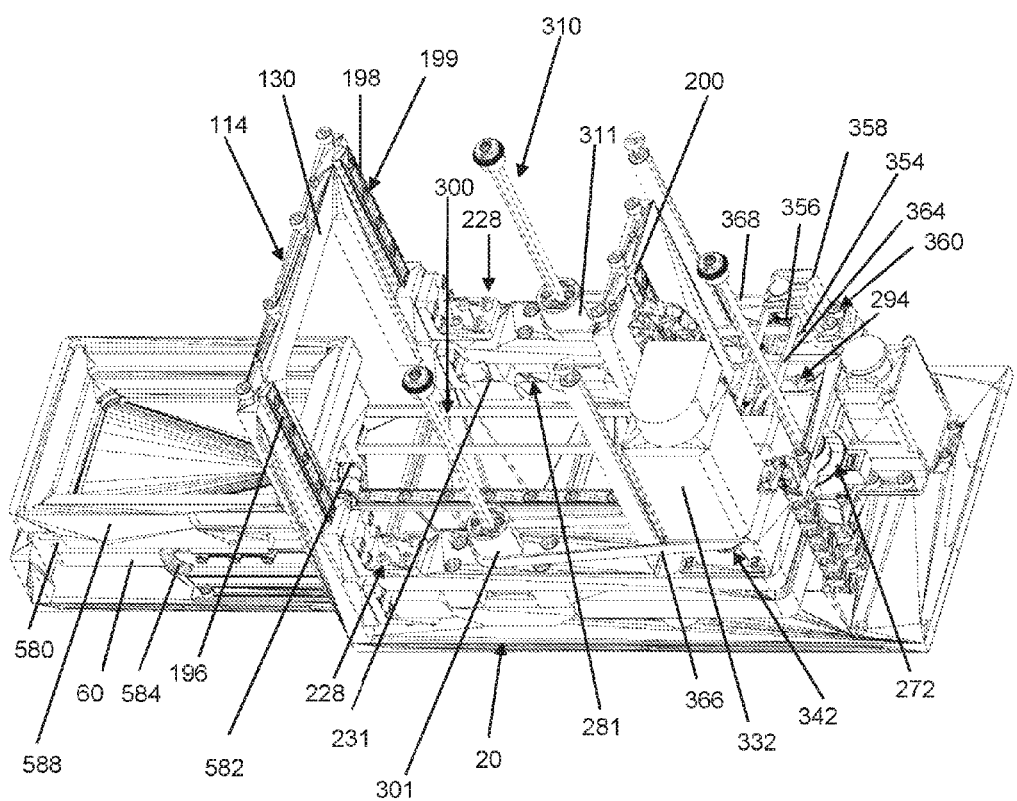
FIG. 9 is a top front longitudinal view detailing the shuttle assembly including a waste tray or trough, the manifold framework assembly, the vertical guide rail assembly, and the tiered elevator lift assembly of the automated positive pressure SPE apparatus.
Figure 10:
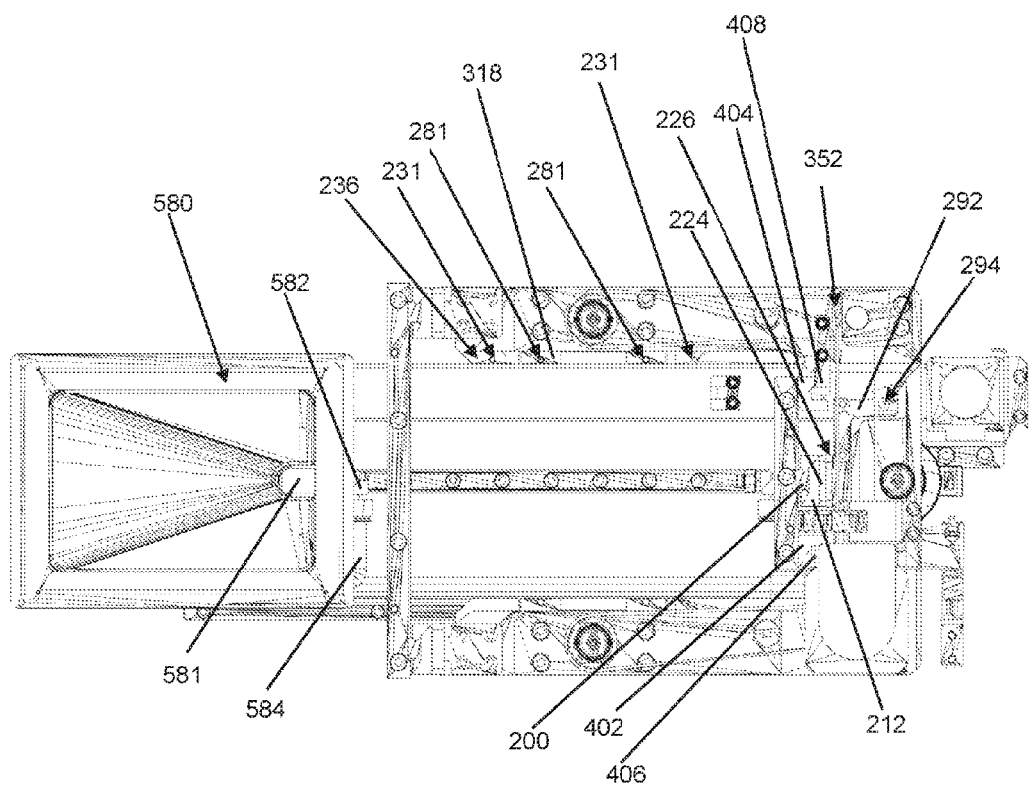
FIG. 10 is a top plan view detailing the shuttle assembly including the waste tray, the manifold framework assembly, the vertical guide rail assembly, and the tiered elevator lift assembly of the automated positive pressure SPE apparatus.

Referring to FIGS. 7, 9, and 10, the waste tray assembly 560 comprises a waste tray 580 located on shuttle 60 via locating pins in the waste tray mating with locating apertures in the shuttle 60. The waste tray 580 having an interior floor with a posteriorly downwardly tapering portion leading to a waste try outlet 581 extending through the posterior wall of waste tray 580 and operatively coupling with elbow fitting 582. In turn, elbow fitting 582 is operatively coupled to one end of a flexible line 584 as illustrated in FIG. 10.

The flexible line 584 moves with the waste tray 580 and line 584 has an opposing end in open fluid coupling communication with the waste line 562 of the waste assembly 560 (FIG. 3).

Additionally, waste tray 580 comprises two pair of side ears 585 with pairs disposed on opposing longitudinal sides of the waste tray with locator receiving apertures 586 disposed in the rear longitudinal pair of side ears 585 which are captured by the lower tiered lift device 230 and in particular by one or more mating pins 231 disposed on an interior ledge support member 236 being received within an underside apertures 586 disposed in the rear longitudinal pair of side ears 585 as controllably aligned by the shuttle 60.

Filter and Collection Plates

Additionally, and referring to FIG. 7 through 10, a filter plate fitting ring 588 surmounts and circumscribes waste tray 580 and is provided with an overhang 589 on each side which is captured by the upper tiered lift device 280 and in particular by one or more mating pins 281 disposed on an interior ledge "U" shaped member 318 being received within an underside aperture of the overhang 589 as controllably aligned when the shuttle 60 is positioning, for example, a filter plate 590 (FIG. 15) to the upper lift device 280.

Figure 28:
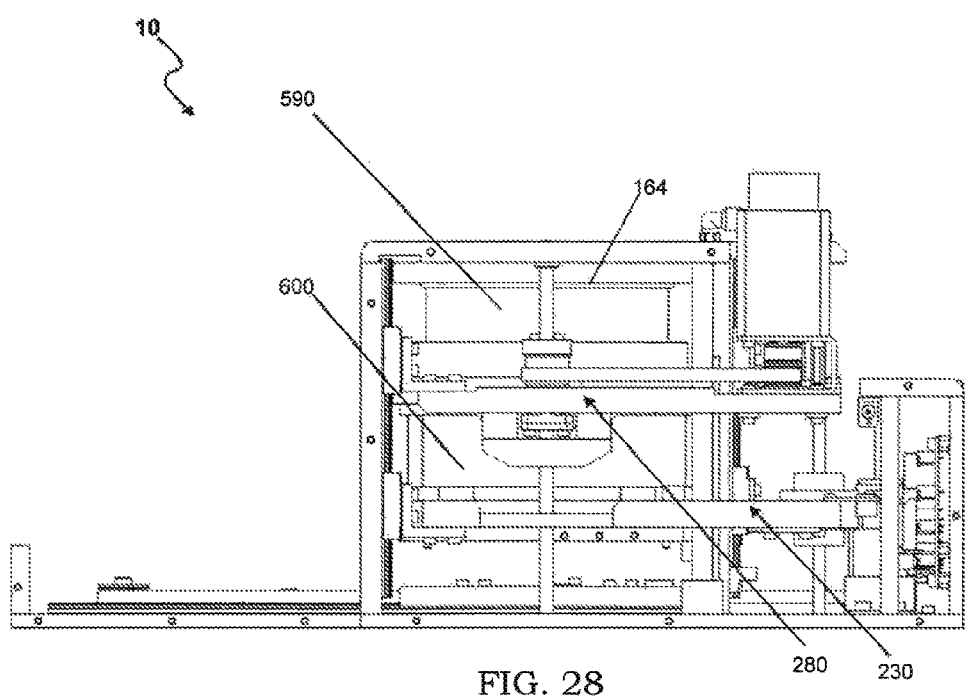
FIG. 28 is a front plan view of the automated positive pressure SPE apparatus shown with the filter plate with the elution agent therein engaged with the manifold by the upper elevator and further shown with the collection plate engaged with the filter plate wherein the nozzles of the filter plate aligned with wells of the collection plate to preclude cross-contamination.

Furthermore, collection plate 600 is configured to surmount the waste tray 580 and be lifted therewith by the lower lift device 230 presenting it, for example, to the filter plate 590 with a controllable height H between collection plate 600 and the filter plate 590 as is illustrated in FIG. 28.

Tiered Elevator Lift Assembly

Referring to FIG. 1, and as noted above, the positive pressure solid phase extraction (SPE) apparatus 10 further comprises the tiered elevator lift assembly 192. Tiered elevator lift assembly 192 comprises the upper lift device 280, the lower lift device 230, and vertical guide rail assembly comprising three triangularly disposed vertical trackways 196, 198, and 200 (FIGS. 4 and 9).

Vertical Guide Rail Assembly

Referring to FIGS. 4 and 5, the vertical guide rail assembly comprises three triangularly disposed vertical trackways 196, 198, and 200 each having a predetermined length.

Parallel spaced apart vertical trackways 196, 198 are respectively disposed on the posterior or interior surfaces of vertical main frame members 124, 126 in a plane parallel to vertical axis 144 of vertical support plate 114 and perpendicular to central longitudinal axis 22 of the base plate 20. Each of the vertical trackways 196, 198 are at an equal latitudinal distance from the central vertical axis 144 and the central longitudinal axis 22 of the base plate 20 and the linear guide rail 46 disposed thereon. Bolts 199 attach the parallel spaced apart vertical trackways 196, 198 to respective posterior surfaces of vertical main frame members 124, 126 of vertical support plate 114 as best illustrated in FIG. 9.

Trackway 200 is disposed on the posterior or interior surface of back central vertical support plate 152 such that the vertical central axis of the trackway 200 is coincident with the central vertical axis 158 of the back central vertical support plate 152. Accordingly, the vertical central axis of the trackway 200 (axis 158) is substantially normal to and coplanar with the central longitudinal axis 22 of the base plate 20 and the linear guide rail 46 that is disposed along central longitudinal axis 22. Additionally, the vertical axis of the three triangularly disposed vertical trackways 196, 198, and 200 are substantially parallel with one another and are spaced apart by a predefined distance.

The guide rail assembly further comprises a pair of bearing guides slideably mounted on each of the vertical trackways 196, 198, and 200 in a vertically tiered fashion. Specifically, a first lower bearing guide 202 and a first upper bearing guide 204 are slideably mounted on trackway 196; a second lower bearing guide 206 and a second upper bearing guide 208 are slideably mounted on trackway 198; and a third lower bearing guide 210 (FIG. 6) and a third upper bearing guide 212 (FIG. 10) are slideably mounted on trackway 200.

As will be further delineated below, the guide rail assembly further comprises six L-shaped lift coupling brackets 214, 216; 218, 220; 222, 224 respectively attached to the six bearing guides 202, 204; 206, 208; and 210, 212 via bolts 226 (FIG. 6) for slideably coupling the lower lift device 230 and the upper lift device 280 to vertical trackways 196, 198, and 200 in a vertically tiered fashion.

Lower Lift Device

Referring to FIG. 5, and in one embodiment, the lower lift device 230 comprises a substantially "U" shaped or forked lower lift member 232. Forked lower lift member 232 comprises laterally spaced longitudinal support members 234, 236 positioned to extend parallel and longitudinally relative to the central axis 22 of the base plate 20 and open towards the shuttle 60 so as to define an open receiving area between the longitudinal support members 234, 236 so dimensioned for unobstructed receipt of shuttle 60 with mounted labware thereon.

Members 234, 236 are respectively provided with clearance openings 238, 240 for receipt of the rods 146, 148 therethrough. Members 234, 236 also employ upper lift bump stops 242, 244.

Additionally, support members 234, 236 of the lower lift member 232 respectively comprise recessed portions 246, 248 for allowing the upper lift device 280 and the lower lift device 230 to mate in a close proximate vertically tiered juxtaposition as illustrated in FIG. 7. In turn, recessed portions 246, 248 respectively comprise clearance openings 250, 252 for lead screws 306 and 316 to extend therethrough unhindered.

Furthermore, support members 234, 236 of the lower lift member 232 respectively comprise terminating ends or guide pads 254, 256 that couple to the vertical guide rails 196 and 198. Specifically, guide pad 254 sits on and is attached to the lower branch of inwardly turned L-shaped lift coupling bracket 214 via a plurality of bolts 226 and, in turn, bracket 214 is bolted via bolts 226 to bearing guide 202 that is slideably coupled to vertical trackway 196 as illustrated in at least FIGS. 5 and 6. Similarly, guide pad 256 sits on and is attached to the lower branch of inwardly turned L-shaped lift coupling bracket 218 via a plurality of bolts and, in turn, bracket 218 is bolted via bolts to bearing guide 206 that is slideably coupled to vertical trackway 198. Additionally, and as illustrated in FIG. 6, a U-shaped bracket 262 is bolted to the underside of the lower lift member 232 via bolts 264 and comprises L-shaped lift coupling bracket 222 bolted to the bearing guide 210 via a plurality of bolts 226 wherein the bearing guide 210 is slideably coupled to vertical trackway 200.

Accordingly, the vertical guide rail assembly provides a three point slideable linkage to the lower elevator device 230.

Linear Actuator

Referring to FIG. 5, the lower lift device 230 further comprises a linear actuator 270 in the form of, but not limited to a stepper motor linear actuator 270.

As illustrated in FIG. 6, the linear actuator 270 comprises a motor assembly 272 mounted to the lower lift member with bolts 274. Referring to FIGS. 1 and 5, the linear actuator 270 comprises a vertical threaded screw 276 fixedly non-rotateably mounted in the top plate 162 of the manifold plate assembly 160 via axial translation preclusion nut 278.

In one embodiment, the motor assembly 272 comprises a reversible motor operatively coupled to a nut that is routed vertically up and down on the threaded screw 276 in response to reversible motor actuation by the controller 400 under orchestration by computer 520 wherein the motor assembly attached lower lift member 232 is vertically raised or lowered by controlled rotation of the motor for obtaining a predetermined or controllable height of the lower lift member 232 and labware mounted thereon. As noted above, the lower lift member 232 is further guided by bearing guide 210 slideably coupling the lower lift member 232 to guide rail 200.

Upper Lift Device

Figure 8:
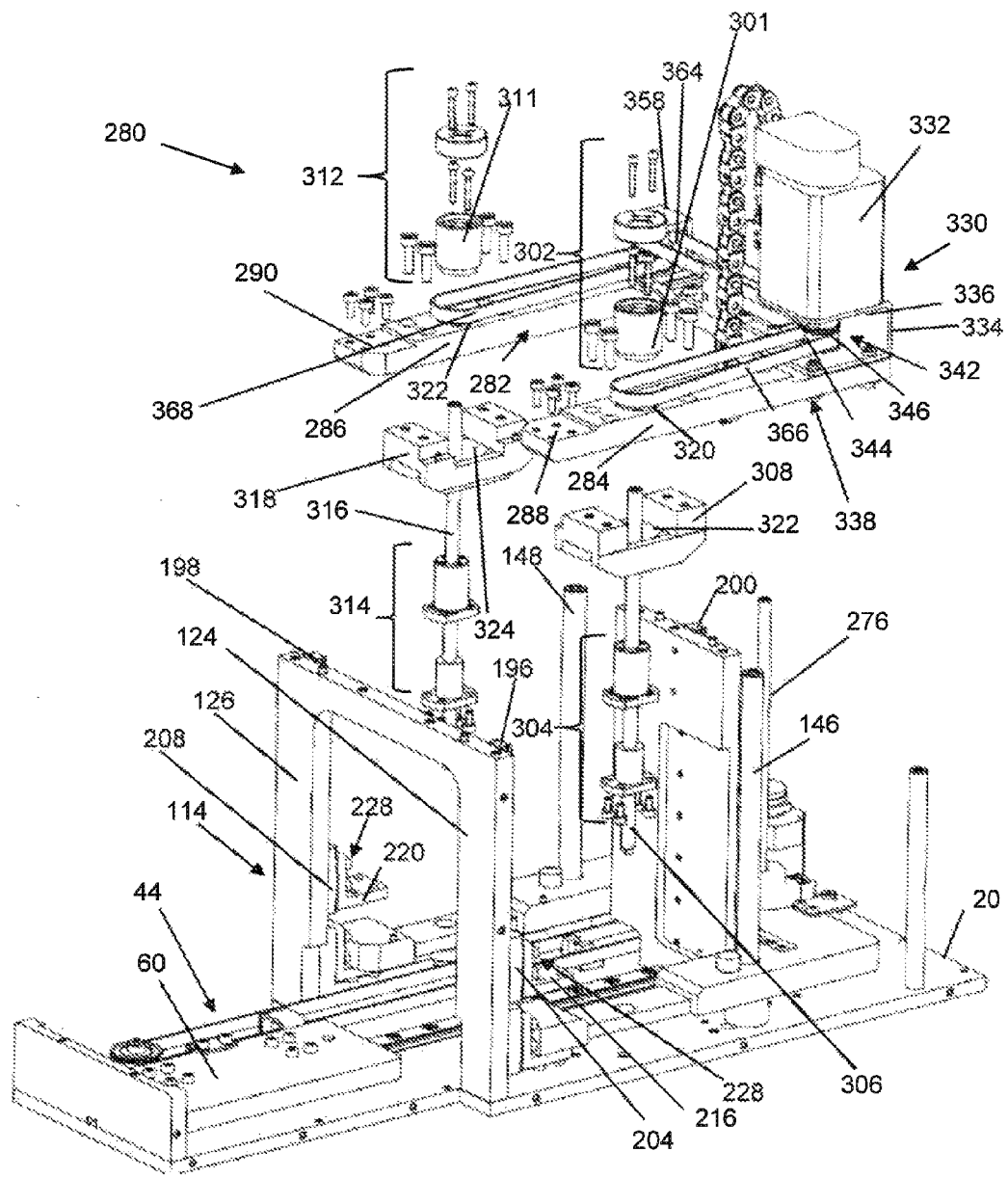
FIG. 8 is a partial exploded parts perspective view detailing an upper tiered lift device and a perspective view illustrating details of the shuttle assembly and the lower lift device of the automated positive pressure SPE apparatus.

Referring now to FIGS. 8 through 10, and in one embodiment, the upper lift device 280 comprises a substantially "U" shaped or forked upper lift member 282, linear actuators 300, 310, a motor assembly 330, cogged pulley assembly comprising a first cogged pulley 342 (FIG. 8) and a second cogged pulley 352 (FIG. 10), and belts 364, 366, and 368.

Forked Upper Lift Member

Forked upper lift member 282 comprises laterally spaced longitudinal support members 284, 286 positioned to extend parallel and longitudinally relative to the central axis 22 of the base plate 20 and open towards the shuttle 60 so as to define an open receiving area between the longitudinal support members 284, 286 so dimensioned for unobstructed receipt of shuttle 60 with mounted labware thereon.

Members 284, 286 are respectively provided with clearance openings for receipt of rods 146, 148 and vertical threaded screw 276 therethrough.

Additionally, support members 284, 286 of the upper lift member 282 respectively comprise terminating ends or guide pads 288, 290 that couple to the vertical guide rails 196, 198. Specifically, guide pad 288 sits on and is attached to the lower branch of inwardly turned L-shaped lift coupling bracket 216 via a plurality of bolts 228 and, in turn, bracket 216 is bolted via bolts 228 to bearing guide 204 that is slideably coupled to vertical trackway 196. Similarly, guide pad 290 sits on and is attached to the lower branch of inwardly turned L-shaped lift coupling bracket 220 via a plurality of bolts 228 and, in turn, bracket 220 is bolted via bolts 228 to bearing guide 208 that is slideably coupled to vertical trackway 198.

Additionally, and as illustrated in FIG. 10, a U-shaped bracket 292 is bolted to the top side of the upper lift member 282 via bolts 294 and comprises L-shaped lift coupling bracket 224 bolted to the bearing guide 212 via a plurality of bolts 226 wherein the bearing guide 212 is slideably coupled to vertical trackway 200. Accordingly, the vertical guide rail assembly provides a three point slideable linkage to the upper elevator device 280.

Linear Actuators

Still referring to FIGS. 8 through 10, the upper lift device 280 further comprises a pair of parallel latitudinally spaced apart vertically extending stepper motor linear actuators 300, 310 (FIG. 9) that are equidistance from central longitudinal axis 22.

Front Actuator

In one embodiment, linear actuator 300 is in the form of a lead nut linear actuator that comprises a lead nut drive pulley assembly 302 surmounting an access aperture 320 in support member 284 of the forked upper lift member 282 that is coaxial with the clearance hole 250 (FIG. 5) in support member 234 of forked lower lift member 232.

Additionally, the linear actuator 300 comprises a lead nut drive pulley interface assembly 304 that passes through aperture 322 in a "U" shaped lead nut bearing support 308 for providing an interfacing coupling with lead nut drive pulley interface assembly 302 that captures support member 284. The lead nut bearing support 308 attaches to the underside of support member 284 and is allowed to mate in a close proximate vertically tiered juxtaposition with support member 234 of the lower lift member 232.

As illustrated, the lead screw 306 operatively passes through both the lead nut drive pulley assembly 302 and the interface assembly 304. At one end, the lead screw 306 is attached to base plate 20 and at the opposing end to top plate 162 via respective axial translation preclusion nuts 278 (FIG. 7).

Rear Actuator

In one embodiment, linear actuator 310 is in the form of a lead nut linear actuator that comprises a lead nut drive pulley assembly 312 surmounting an access aperture 322 in support member 286 of the forked upper lift member 282 that is coaxial with the clearance hole 252 (FIG. 5) in support member 236 of forked lower lift member 232.

Additionally, the linear actuator 310 comprises a lead nut drive pulley interface assembly 314 that passes through aperture 324 in a "U" shaped lead nut bearing support 318 for providing an interfacing coupling with lead nut drive pulley interface assembly 312 that captures support member 286. The lead nut bearing support 318 attaches to the underside of support member 286 and is allowed to mate in a close proximate vertically tiered juxtaposition with support member 236 of the lower lift member 232.

As illustrated, the lead screw 316 operatively passes through both the lead nut drive pulley assembly 312 and the interface assembly 314. One end of lead screw 316 is attached to base plate 20 and the opposing end to top plate 162 via respective axial translation preclusion nuts 278.

Motor Assembly

Referring now to FIGS. 8 and 9, and in one embodiment, the upper lift device 280 further comprises motor assembly 330. Motor assembly 330 comprises reversibly excitable motor 332 mounted proximate a posterior corner of forked upper lift member 282 via a generally "U" shaped motor bracket 334. The generally "U" shaped motor bracket 334 is turned sideways for providing a horizontal landing attaching to motor 332 via motor bolts 336 and a spaced landing attaching to the upper surface of the upper lift device 280 via bolts 338 such that the space between the landings or horizontally extending sides of bracket 334 define a cogged pulley space for receiving a cogged pulley assembly 342 that is operatively coupled to reversibly excitable motor 332 as detailed below.

Cogged Pulley Assembly

Now referring to FIGS. 8 through 10, and as noted above, an embodiment of the upper lift device 280 further comprises a first cogged pulley 342 assembly (FIG. 8) and a second cogged pulley assembly 352 (FIG. 10).

First cogged pulley assembly 342 is received within the cogged pulley space defined by horizontally extending sides of bracket 334 and is operatively coupled to motor 332 for rotation thereby. First cogged pulley assembly 342 comprises a first horizontally disposed lower cogged pulley 344 and a first horizontally disposed upper cogged pulley 346.

Second cogged pulley assembly 352 comprises a second horizontally disposed lower cogged pulley 354 and a second horizontally disposed upper cogged pulley 356 vertically pinned for rotation in a sideways disposed "U" shaped bracket 358. Utilizing bolts 360, bracket 358 is attached to the upper surface of the forked upper lift member 282 at a posterior corner that latitudinally opposes the first cogged pulley 342 for latitudinally aligning the second cogged pulley assembly 352 with the first cogged pulley assembly 342 at a complemental height.

Belts

A first cogged belt 364 is latitudinally passed around the upper cogged pulley 346 of the first cogged pulley assembly 342 and the upper cogged pulley 356 of the second cogged pulley assembly 352.

In turn, a second cogged belt 366 is longitudinally passed around the lower cogged pulley 344 of the first cogged pulley assembly 342 and around a first cogged lead nut drive pulley 301 of the lead nut drive pulley assembly 302.

Likewise, a third cogged belt 368 is longitudinally passed around the lower cogged pulley 354 of the second cogged pulley assembly 352 and around a second cogged lead nut drive pulley 311 of the lead nut drive pulley assembly 312.

The respective upper and lower cogged pulleys are rotateably fixed together such that the motor drives the upper and lower cogged pulley 346, 344 in unison and such that the upper and lower cogged pulleys 356, 354 are also driven in unison.

Accordingly, directional rotational actuation of the single motor 332 results in the simultaneous liner actuation of linear actuators 300, 310 for raising and lowering the forked upper lift member 282 with the motor 332 onboard thereof.

Specifically, when motor 332 is actuated, the lower cogged pulley 344 and the upper cogged pulley 346 are driven thereby translating motion to the cogged belt 366 for driving the first cogged lead nut drive pulley 301 while simultaneously driving the second cogged lead nut drive pulley 311 with the cogged belt 368 receiving motion from the second lower cogged pulley 354 which, in turn, receives motion from the second upper cogged pulley 356 receiving motion by cogged belt 364 being driven by the first upper cogged pulley 346 for vertically raising and lowering the forked upper lift member 282 with the motor 332 onboard by transforming the rotation of the motor to the liner actuation of linear actuators 300, 310 wherein the forked upper lift member 282 is raised and lowered in a substantially horizontal plane substantially parallel with base plate 20 and top plate 160.

Figure 11:
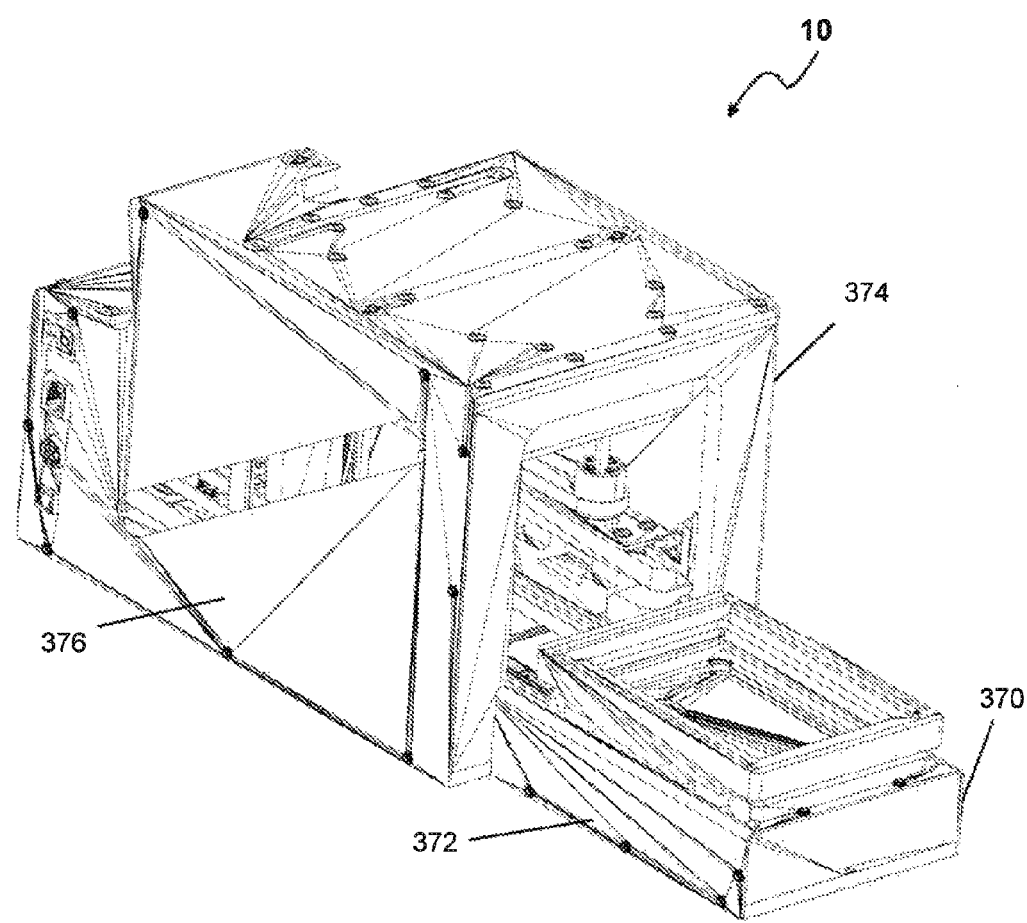
FIG. 11 is a forward lateral end and rear longitudinal side perspective view of the automated positive pressure SPE apparatus illustrated further with a pair of forward and a pair of rearward longitudinal side plates.

In one embodiment, and as illustrated in FIG. 11, apparatus 10 further comprises a pair of forward longitudinal side protective plates 370, 372 and a pair of rearward longitudinal side protective plates 374, 376.

Use and Operation

The use and operation of apparatus 10 will be further delineated by an example, but it is to be understood that multiple positive pressure SPE processes are completed along with multiple plate management scenarios being solved and provided by the two tier plate mounting scheme of the shuttle 60.

Figure 12:
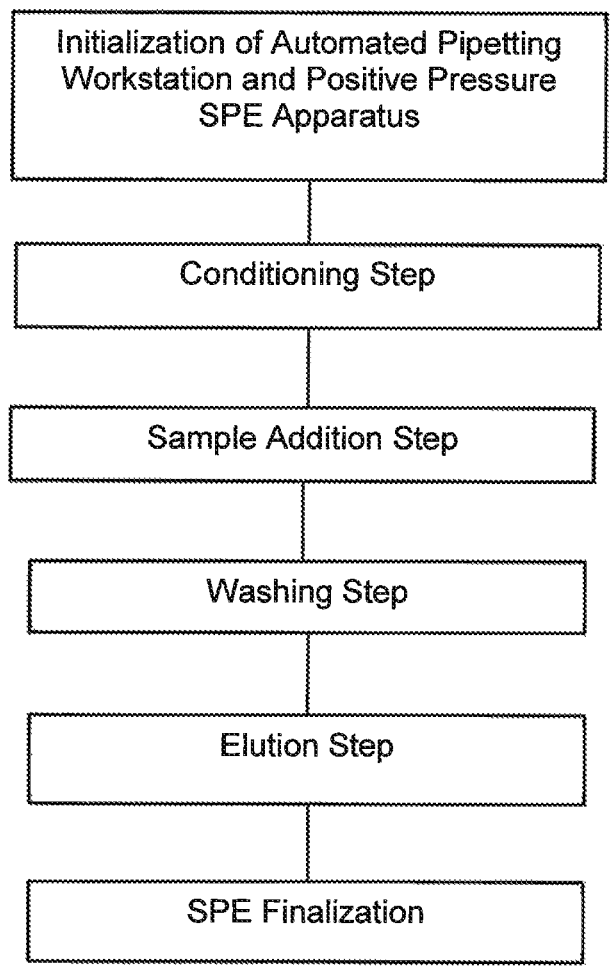
FIG. 12 is a general flow chart of an embodiment of an automated positive pressure SPE sequencing process of the automated positive pressure SPE apparatus.

Accordingly, reference is made to FIG. 12 for outlining this positive pressure SPE process example with FIG. 13 providing further details thereof which are diagrammatically illustrated in FIGS. 14 through 30 described below.

Figure 14:
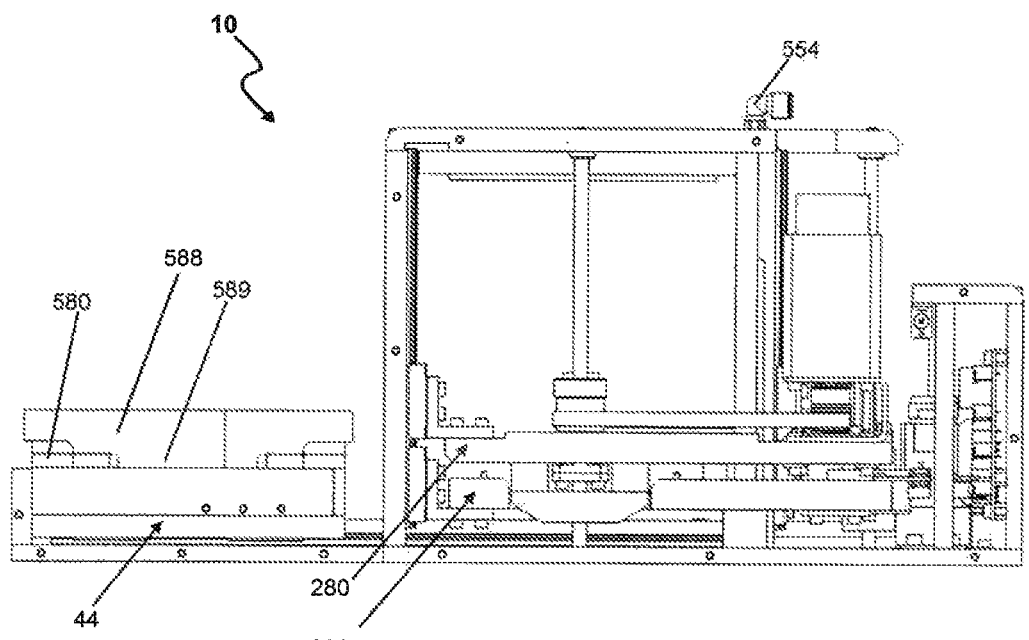
FIG. 14 is a front plan view of the automated positive pressure SPE apparatus shown in an initialized state.

At the outset, FIG. 14 illustrates the automated positive pressure SPE apparatus 10 in an initialized state with the lower and upper lifts 230, 280 in a lower initial loading position and the shuttle assembly 44 in the home position surmounted by a waste tray 580 which is, in turn, surmounted by filter plate fitting ring 588 having overhang 589.

Figure 15:
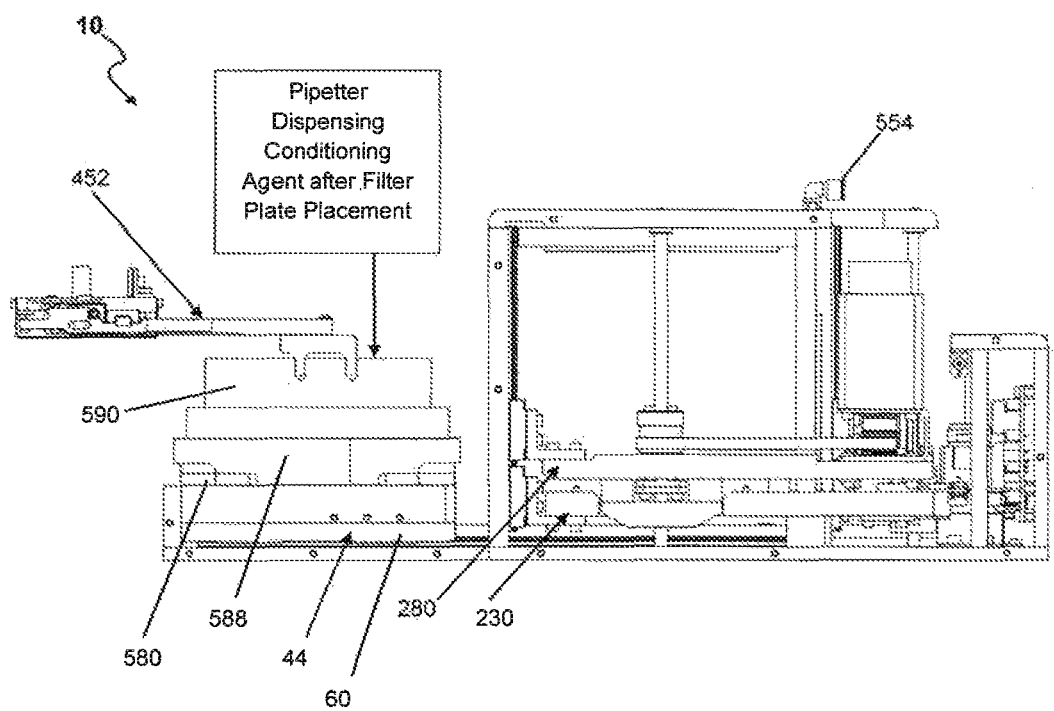
FIG. 15 is a front plan view of the automated positive pressure SPE apparatus shown receiving labware in the form of a filter plate from the gripper of the automated pipetting workstation wherein the filter plate is tiered above and mates with the waste tray that is mounted on the shuttle assembly located at an accessible position of the gripper and pipetter or probe head assembly of the automated pipetting workstation for locating the filter plate and performing a conditioning step comprising dispensing a conditioning agent into the filter plate at the accessible position while capturing all fluids which are pushed through the filter plate in the conditioning step.

FIG. 15 illustrates the automated positive pressure SPE apparatus 10 receiving labware in the form of a filter plate 590 from the engaging fingers or gripper 452 of the automated pipetting workstation 420 wherein the filter plate 590 is tiered above and mates with, via the filter plate fitting ring 588, the waste tray 580 that is mounted on the shuttle 60 of the shuttle assembly 44 located at the accessible position of the gripper and pipetter or probe head assembly of the automated pipetting workstation 420 for locating the filter plate and performing a conditioning step comprising dispensing a conditioning agent into the filter plate 590 at the accessible position while capturing all fluids which are pushed through the filter plate 590 in the conditioning step.

Figure 16:
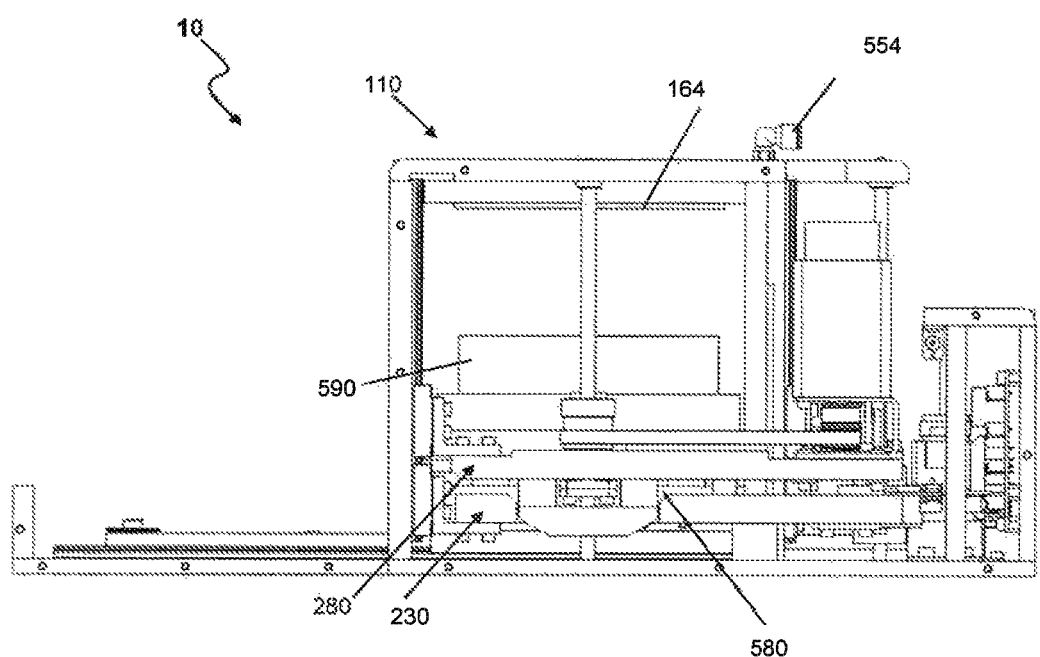
FIG. 16 is a front plan view of the automated positive pressure SPE apparatus shown with the shuttle assembly transported within the elevated manifold assembly and the filter plate positioned via sensors over locating pins of the upper elevator device to ensure positional accuracy while the filter plate is being lifted up to engage the manifold while simultaneously presenting the waste tray over locating pins of the lower elevator device to ensure positional accuracy while the waste tray is being lifted up to engage under the filter plate engaged under the manifold plate.

FIG. 16 illustrates the automated positive pressure SPE apparatus 10 with the shuttle assembly 44 transported within the elevated manifold assembly 110 and the filter plate 590 positioned via sensors described above over locating pins of the upper elevator device 280 to ensure positional accuracy while the filter plate 590 is being lifted up to engage the manifold 164 while simultaneously presenting the waste tray over locating pins of the lower elevator device 230 to ensure positional accuracy while the waste tray 580 is being lifted up to engage under the filter plate 590 engaged under the manifold plate 164.

Figure 17:
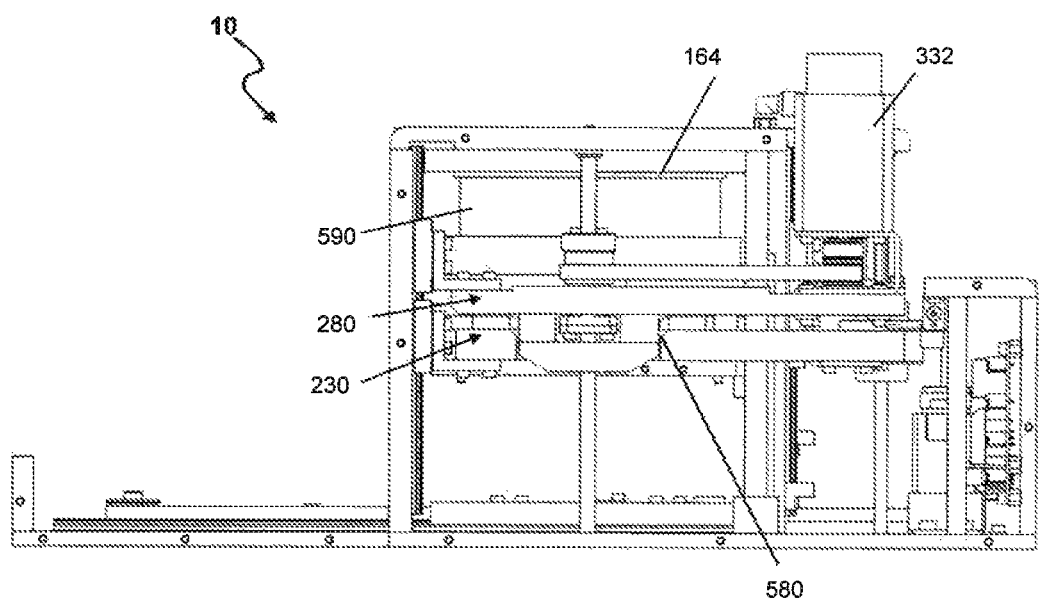
FIG. 17 is a front plan view of the automated positive pressure SPE apparatus shown presenting the filter plate to the manifold plate with the upper elevator and positioning the waste tray with the lower elevator during the conditioning phase.

FIG. 17 illustrates the automated positive pressure SPE apparatus 10 presenting the filter plate 590 to the manifold plate 164 with the upper elevator 280 and positioning the waste tray 580 with the lower elevator device 230 during the conditioning phase. In one embodiment, the shuttle, with the waste tray 580, remains in the elevator framework while the filter plate 590 is being lifted. Once the filter plate 590 has been positioned against the manifold plate 164 the waste tray 580 is then brought up beneath the filter plate 590 via the lower lift device 230. Positive pressure is then applied to the manifold 164 which in turn pushes the conditioning fluid out of the filter plate 590 into the waste tray 580. The waste fluid is then siphoned out of the apparatus 10.

Figure 18:
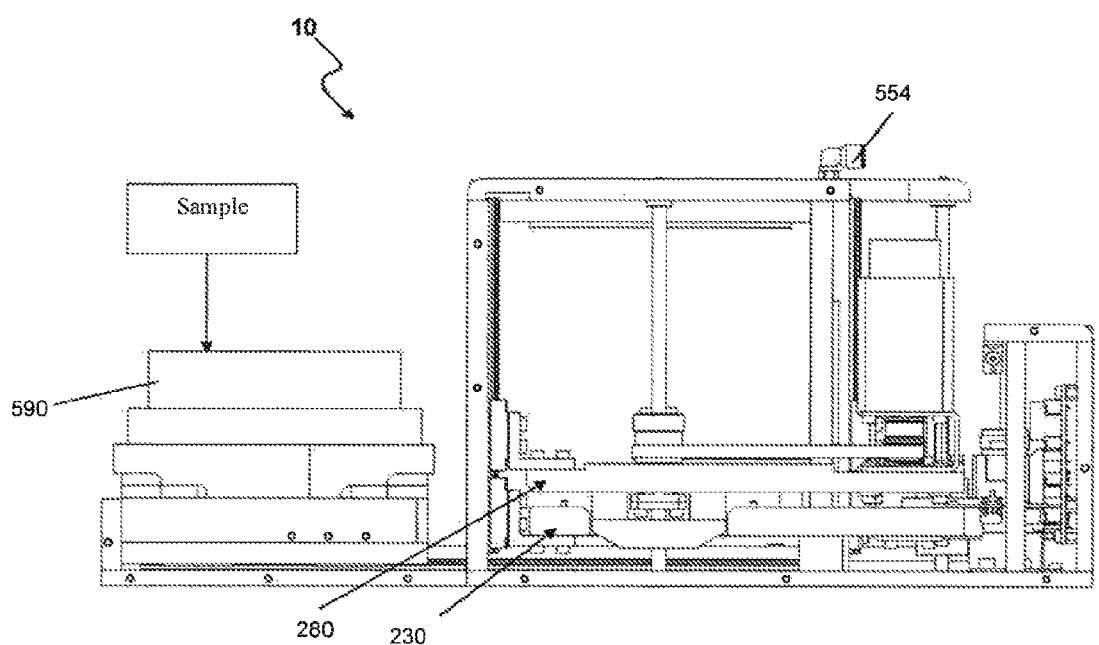
FIG. 18 is a front plan view of the automated positive pressure SPE apparatus shown with the filter plate repositioned back to the automated pipetting workstation accessible position and the elevator assemblies down with the condition process completed to allow the pipetter to dispense the sample to be separated into the filter plate.

FIG. 18 illustrates the automated positive pressure SPE apparatus 10 with the filter plate 590 repositioned back to the automated pipetting workstation accessible position and the elevator assemblies 230, 280 down with the condition process completed to allow the pipetter to dispense the sample to be separated into the filter plate 590.

Figure 19:
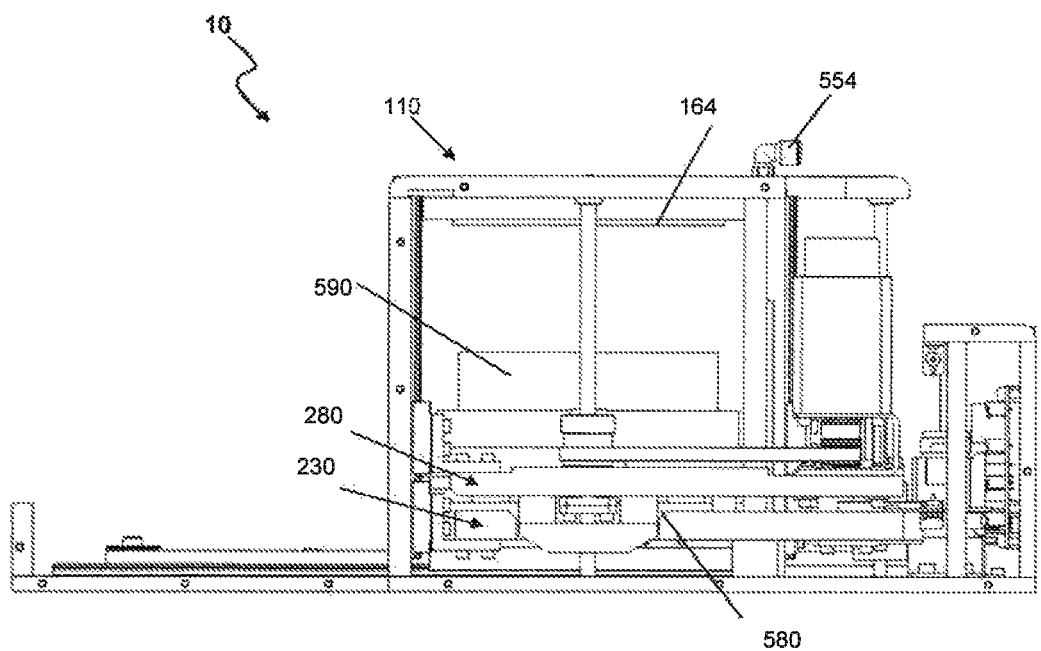
FIG. 19 is a front plan view of the automated positive pressure SPE apparatus shown with the shuttle assembly transported back within the elevated manifold assembly and the filter plate positioned via sensors over locating pins of the upper elevator device to ensure positional accuracy while the filter plate is being lifted up to engage the manifold while simultaneously presenting the waste tray over locating pins of the lower elevator device to ensure positional accuracy while the waste tray is being lifted up to engage under the filter plate engaged under the manifold plate.

FIG. 19 illustrates the automated positive pressure SPE apparatus 10 with the shuttle assembly 44 transported back within the elevated manifold assembly 110 and the filter plate 590 positioned via sensors over locating pins of the upper elevator device 280 to ensure positional accuracy while the filter plate 590 is being lifted up to engage the manifold 164 while simultaneously presenting the waste tray 580 over locating pins of the lower elevator device 230 to ensure positional accuracy while the waste tray 580 is being lifted up to engage under the filter plate 590 engaged under the manifold plate 164.

Figure 20:
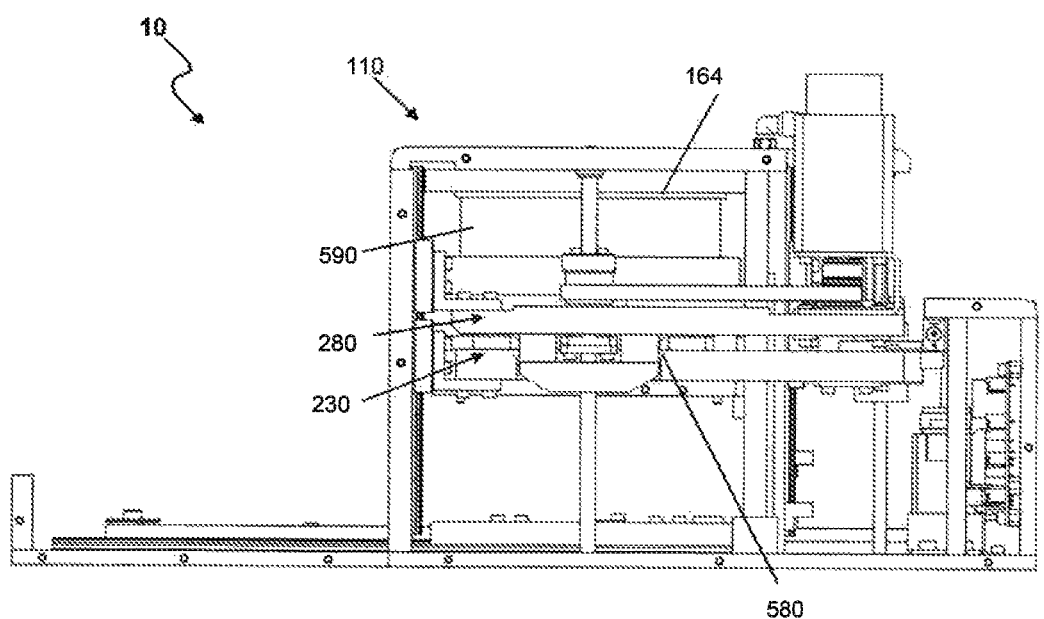
FIG. 20 is a front plan view of the automated positive pressure SPE apparatus shown presenting the filter plate with the sample therein to the manifold with the upper elevator and positioning the waste trough with the lower elevator during the sample addition phase.

FIG. 20 illustrates the automated positive pressure SPE apparatus 10 presenting the filter plate 590 with the sample therein to the manifold 164 with the upper elevator device 280 and positioning the waste trough 580 with the lower elevator device 230 during the sample addition phase. In one embodiment, the shuttle assembly 44, with the waste tray 580, remains in the elevator framework 110 while the filter plate 580 with the sample therein is being lifted. Once the filter plate 580 has been positioned against the manifold plate 164 the waste tray 580 is then brought up beneath the filter plate 590 via the lower elevator device 230. Positive pressure is then applied to the manifold 164 and the waste fluid is then siphoned out of the apparatus 10.

Figure 21:
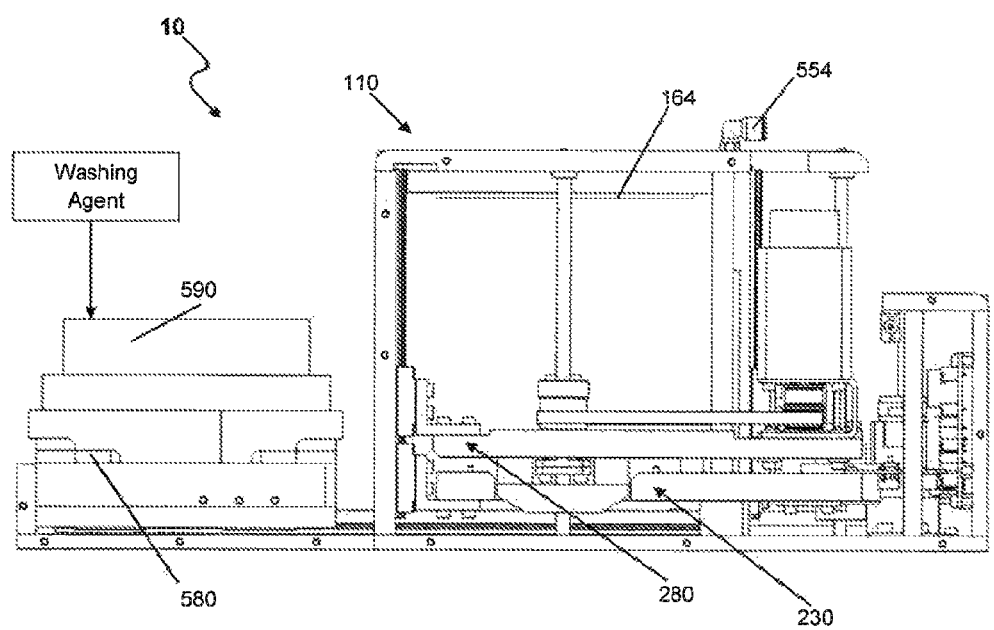
FIG. 21 is a front plan view of the automated positive pressure SPE apparatus shown with the filter plate repositioned back to the automated pipetting workstation accessible position and the elevator assemblies down to allow the pipetter to dispense the washing agent into the filter plate.

FIG. 21 illustrates the automated positive pressure SPE apparatus 10 with the filter plate 590 repositioned back to the automated pipetting workstation accessible position and the elevator assemblies 230, 280 down to allow the pipetter to dispense a washing agent into the filter plate 590.

Figure 22:
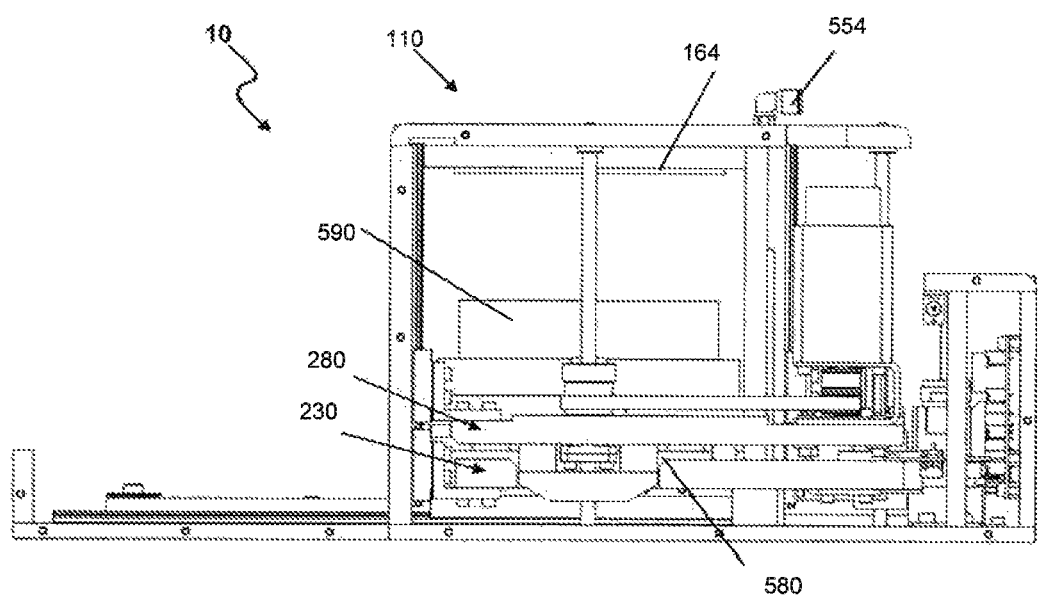
FIG. 22 is a front plan view of the automated positive pressure SPE apparatus shown with the shuttle assembly transported back within the elevated manifold assembly and the filter plate with the washing agent positioned via sensors over locating pins of the upper elevator device to ensure positional accuracy while the filter plate is being lifted up to engage the manifold plate while simultaneously presenting the waste tray over locating pins of the lower elevator device to ensure positional accuracy while the waste tray is being lifted up to engage under the filter plate engaged under the manifold plate.

FIG. 22 illustrates the automated positive pressure SPE apparatus 10 with the shuttle transported back within the elevated manifold assembly 110 and the filter plate 590 with the washing agent positioned via sensors over locating pins of the upper elevator assembly 280 to ensure positional accuracy while the filter plate 590 is being lifted up to engage the manifold plate 164 while simultaneously presenting the waste tray 580 over locating pins of the lower elevator device 230 to ensure positional accuracy while the waste tray 580 is being lifted up to engage under the filter plate 590 engaged under the manifold plate 164.

Figure 23:
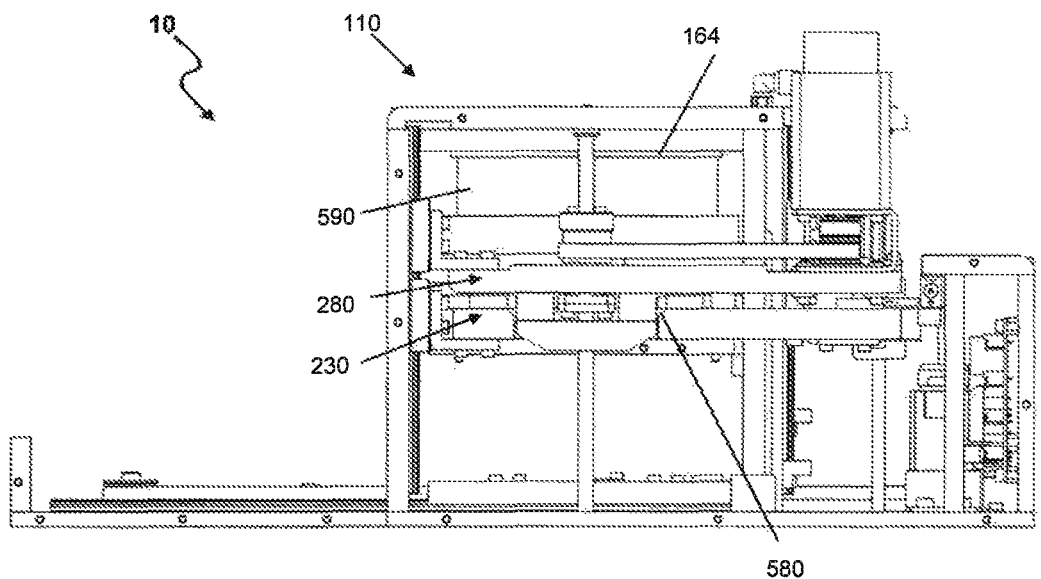
FIG. 23 is a front plan view of the automated positive pressure SPE apparatus shown presenting the filter plate with the washing agent therein to the manifold with the upper elevator and positioning the waste trough with the lower elevator during the washing phase.

FIG. 23 illustrates the automated positive pressure SPE apparatus 10 presenting the filter plate 590 with the washing agent therein to the manifold 164 with the upper elevator device 280 and positioning the waste tray 580 with the lower elevator device 230 during the washing phase. In one embodiment, the shuttle assembly 44, with the waste tray 580, remains in the elevator framework 110 while the filter plate 590 with the washing agent therein is lifted. Once the filter plate 590 is positioned against the manifold plate 164 the waste tray 580 is then brought up beneath the filter plate 590 via the lower lift device 230. Positive pressure is then applied to the manifold and the waste fluid is then siphoned out of the apparatus 10.

Figure 24:
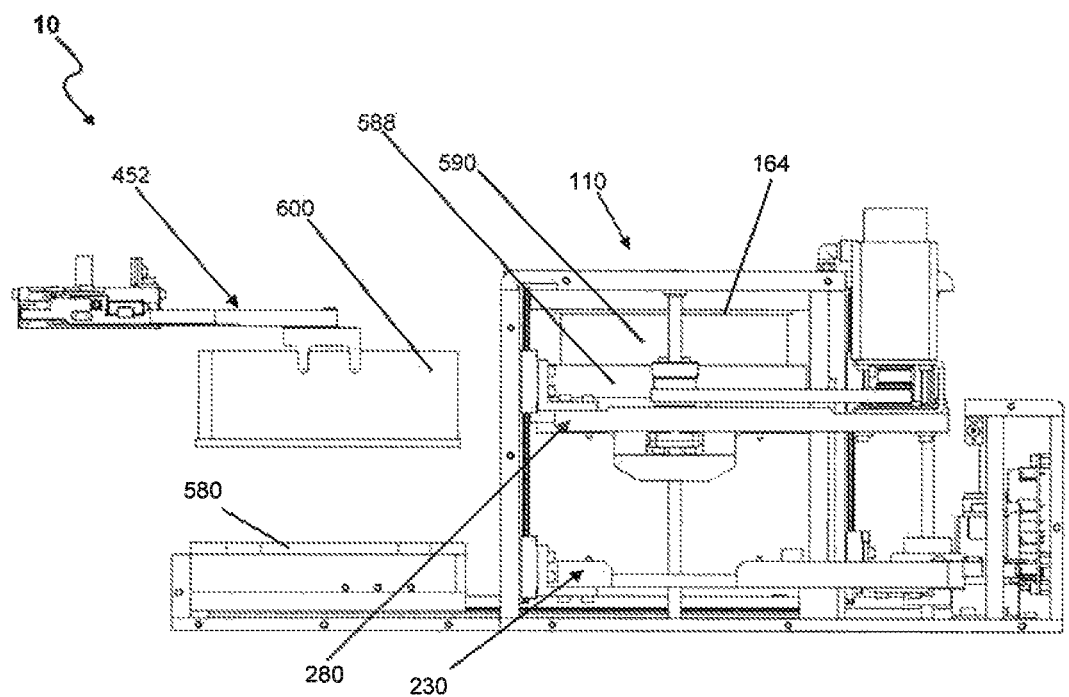
FIG. 24 is a front plan view of the automated positive pressure SPE apparatus shown with the lower elevator at the at home position, the shuttle assembly with the waste tray repositioned back to the automated pipetting workstation accessible position or the shuttle assembly home to allow the pipetter to place the collection plate on the shuttle assembly while the upper elevator device maintains the vertical abutment of the filter plate, with the remaining sample therein, below the manifold plate.

FIG. 24 illustrates the automated positive pressure SPE apparatus 10 with the lower elevator device 230 at the home position, the shuttle assembly with the waste tray 580 repositioned back to the automated pipetting workstation accessible position or the shuttle home to allow the pipetter to place the collection plate 600 on the shuttle while the upper elevator device 280 maintains the vertical abutment of the filter plate 590, with the remaining sample therein, below the manifold plate 164.

Figure 25:
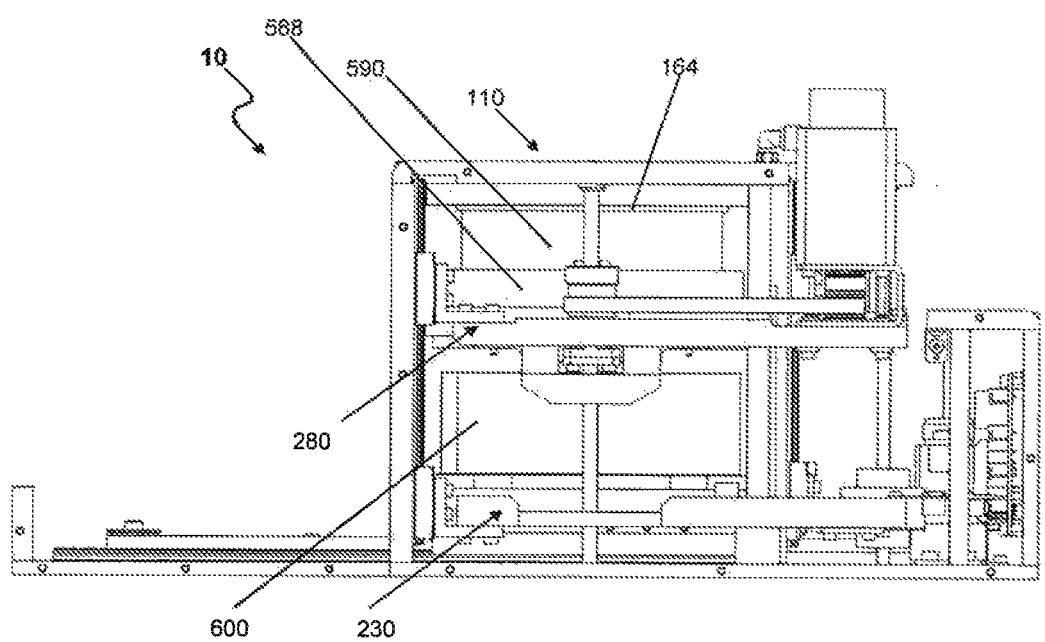
FIG. 25 is a front plan view of the automated positive pressure SPE apparatus shown with the collection plate transported within the elevated manifold assembly and positioned via sensors over locating pins of the lower elevator device to ensure positional accuracy while the collection plate is being lifted up to engage under the filter plate engaged under the manifold plate to allow the upper elevator device to lower the filter plate onto the collection plate.

FIG. 25 illustrates the automated positive pressure SPE apparatus 10 with the collection plate 600 transported within the elevated manifold assembly 110 and positioned via sensors over locating pins of the lower elevator device 230 to ensure positional accuracy while the collection plate 600 is being lifted up to engage under the filter plate 590 engaged under the manifold plate 164 to allow the upper elevator device 280 to lower the filter plate onto the collection plate 600.

Figure 26:
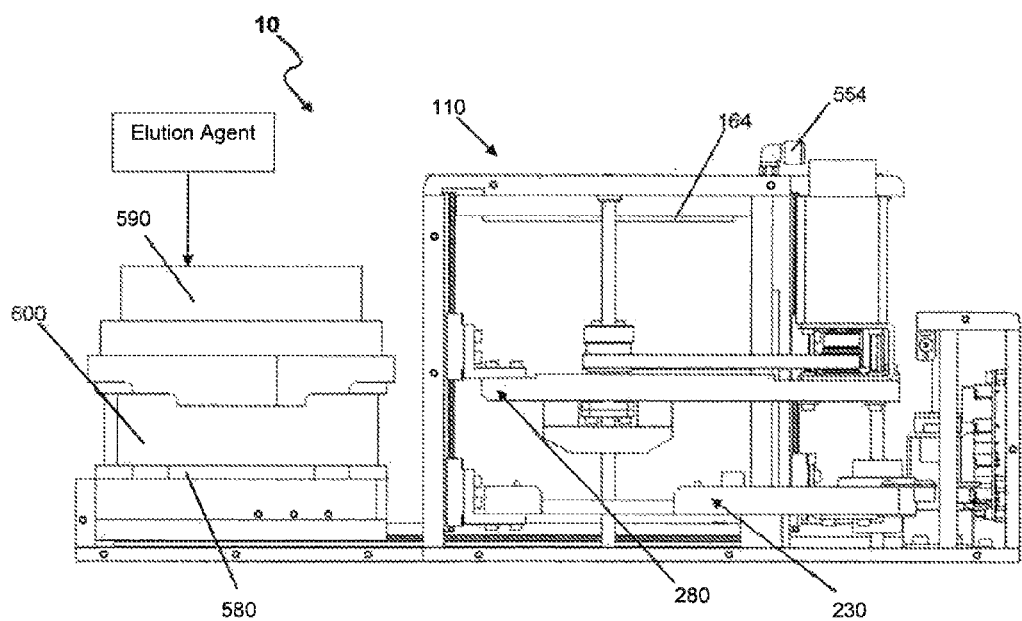
FIG. 26 is a front plan view of the automated positive pressure SPE apparatus shown with the elevator assemblies in relatively down positions with the shuttle assembly transported back to the automated pipetting workstation accessible position with both the collection plate and filter plate thereon to allow the pipetter to dispense an elution agent to the filter plate.

FIG. 26 illustrates the automated positive pressure SPE apparatus 10 with the elevator assemblies 230, 280 in relatively down positions with the shuttle assembly 44 transported back to the automated pipetting workstation accessible position with both the collection plate 600 and filter plate 590 thereon to allow the pipetter to dispense an elution agent to the filter plate 590.

Figure 27:
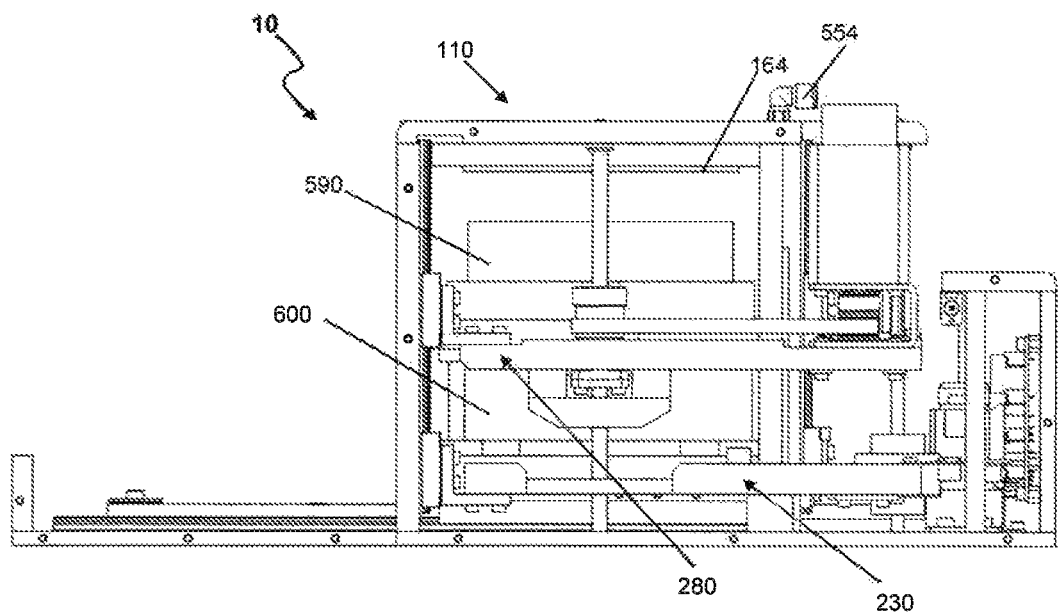
FIG. 27 is a front plan view of the automated positive pressure SPE apparatus shown with the shuttle assembly and both the collection plate and filter plate with the elution agent disposed thereon transported within the elevated manifold assembly with the filter plate with the elution agent positioned via sensors over locating pins of the upper elevator device to ensure positional accuracy while the filter plate is being lifted up to engage the manifold plate while simultaneously presenting the collection plate over locating pins of the lower elevator device to ensure positional accuracy while the collection plate is being lifted up to engage the nozzles on the filter plate which, in turn, is engaged under the manifold plate.

FIG. 27 illustrates the automated positive pressure SPE apparatus 10 with the shuttle assembly 44 and both the collection plate 600 and filter plate 590 comprising elution agent disposed thereon transported within the elevated manifold assembly 110 with the filter plate 590 comprising elution agent positioned via sensors over locating pins of the upper elevator device 280 to ensure positional accuracy while the filter plate 590 is being lifted up to engage the manifold plate 164 while simultaneously presenting the collection plate 600 over locating pins of the lower elevator assembly to ensure positional accuracy while the collection plate 600 is being lifted up to engage the nozzles on the filter plate which, in turn, is engaged under the manifold plate 164.

FIG. 28 illustrates the automated positive pressure SPE apparatus 10 with the filter plate 590 with the elution agent therein engaged with the manifold 164 by the upper elevator device 280 and further shown with the collection plate 600 engaged with the filter plate 590 wherein the nozzles of the filter plate aligned with wells of the collection plate to preclude cross-contamination.

Figure 29:
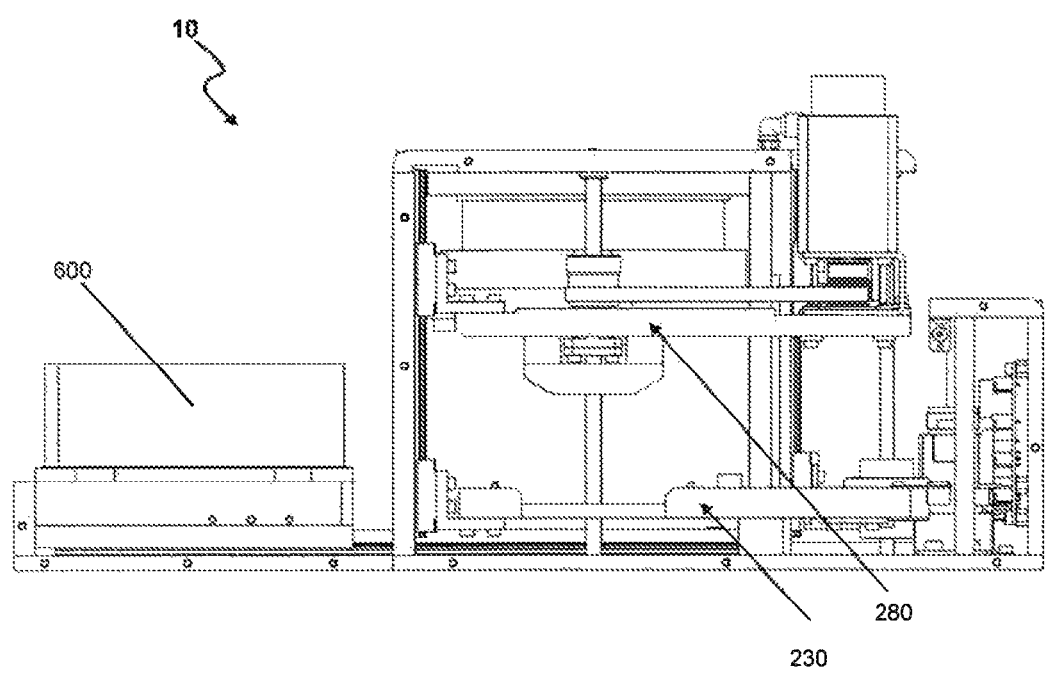
FIG. 29 is a front plan view of the automated positive pressure SPE apparatus shown with the collection plate shuttled back to the automated pipetting workstation accessible position to allow the pipetter to remove the collection plate from the shuttle.

FIG. 29 illustrates the automated positive pressure SPE apparatus 10 with the collection plate 600 shuttled back to the automated pipetting workstation accessible position to allow the pipetter to remove the collection plate 600 from the shuttle assembly 44.

Figure 30:
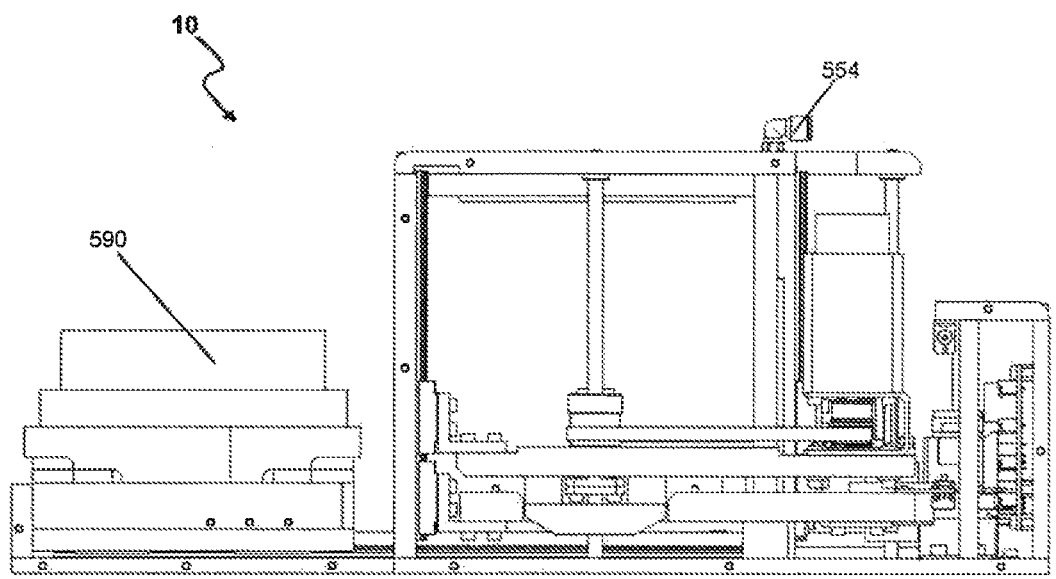
FIG. 30 is a front plan view of the automated positive pressure solid phase extraction apparatus shown presenting the filter plate back to the automated pipetting workstation accessible position to allow the pipetter to remove the filter plate from the shuttle.

FIG. 30 illustrates the automated positive pressure solid phase extraction apparatus 10 presenting the filter plate 590 back to the automated pipetting workstation accessible position to allow the pipetter to remove the filter plate 590 from the shuttle assembly 44.

Accordingly, and in one aspect, the upper and lower lift members and the shuttle are individually controlled for vertically shuttling labware into the tiered elevator lift assembly and respectively handing it off to the upper and lower lifts tiered lift devices of the tiered elevator lift assembly for lifting one labware piece or two tiered labware pieces up to the manifold plate for processing while simultaneously displacing the shuttle back to the gripper and pipetter/probe head assembly accessible home position in accordance with the steps of the current user defined or predefined SPE process.

Examples of the automated pipetting workstations including software are presently manufactured and sold by the assignee of the present patent application, Hamilton Company, 4970 Energy Way, Reno, Nev. 89502, United States Of America.

Figure 31:
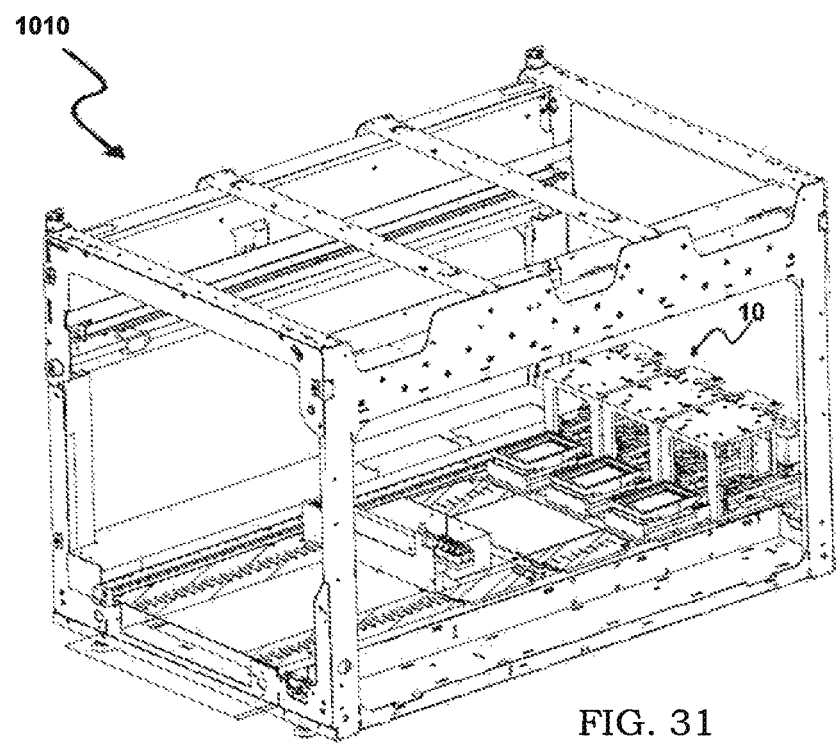
FIG. 31 is a perspective view illustrating a plurality of the automated positive pressure SPE apparatuses disposed on a rear lateral deck portion of another embodiment of an automated pipetting workstation only framework of which is illustrated for clarity of illustration of each SPE apparatus disposed on the deck.

FIG. 31 is a perspective view illustrating a plurality of the automated positive pressure SPE apparatuses 10 disposed on a rear lateral deck portion of another embodiment of an automated pipetting workstation 1010 only framework of which is illustrated for clarity of illustration of each SPE apparatus 10 disposed on the deck.

Evaporator

Referring to FIG. 32, and in another aspect, an embodiment of the invention provides an automated positive pressure SPE apparatus 10 further comprising a heater control unit 700 for adding heat to the system air for serving as an evaporator for downstream SPE processes.

Figure 33:
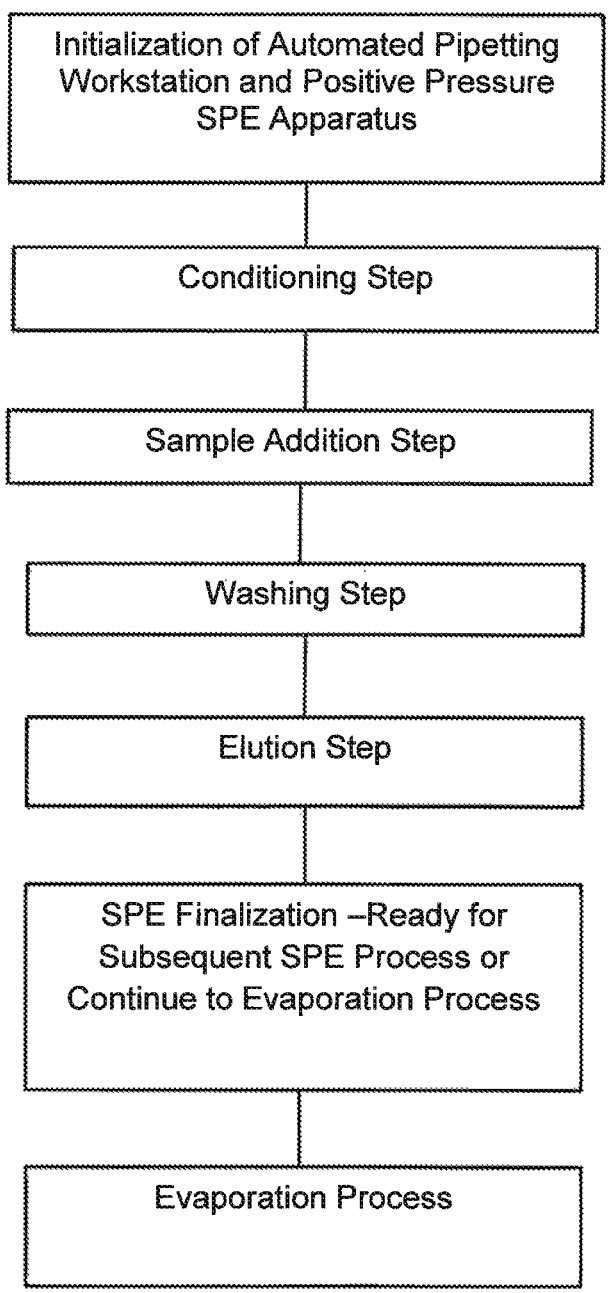
FIG. 33 is a general flow diagram of an embodiment of an automated positive pressure SPE sequencing process of the automated positive pressure SPE apparatus further comprising an evaporation process.

Referring to FIG. 33, a general flow diagram of an embodiment of an automated positive pressure SPE process is illustrated further comprising an evaporation process that is detailed in FIG. 34 and diagrammatically illustrated in FIGS. 35 through 42.

As described above, software controls the automated pipetting workstation 420 and positive pressure solid phase extraction apparatus 10.

Figure 35:
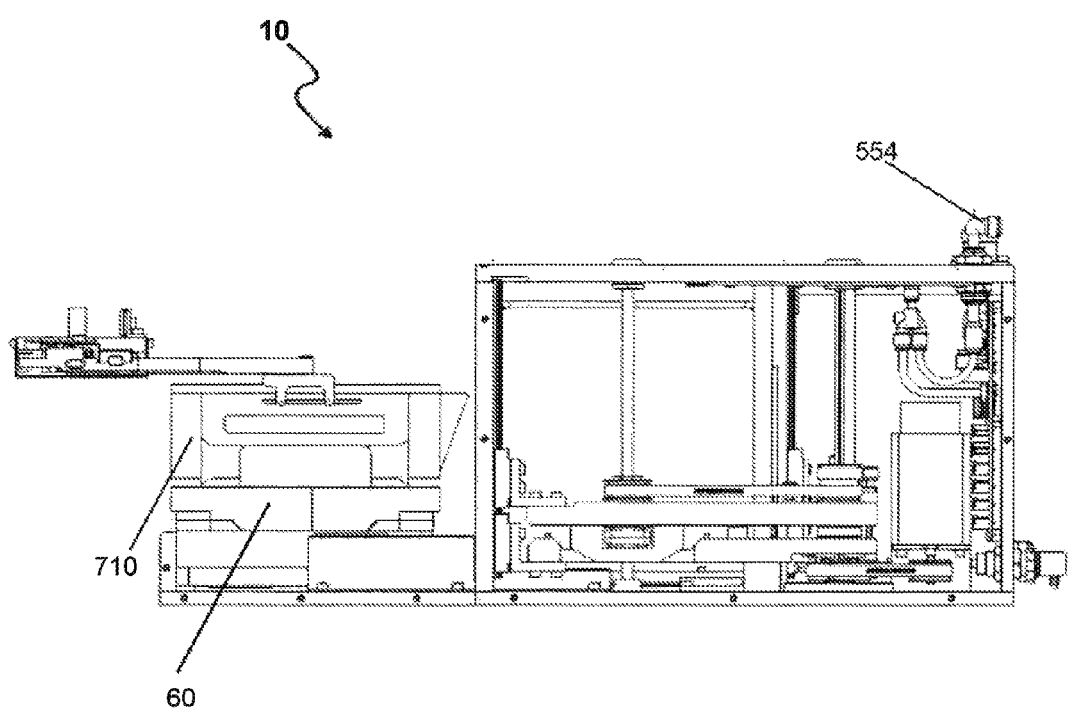
FIG. 35 is a front plan view of the automated positive pressure SPE apparatus shown receiving an evaporator adapter from the automated pipetting workstation during the evaporation process.

Referring to FIGS. 34 and 35, and at the outset of the evaporation process, the automated pipetting workstation 420 is software controlled to place an evaporator adapter 710 onto the shuttle 60 of the positive pressure solid phase extraction apparatus 10 thereby receiving by apparatus 10 the evaporator adapter 710 from the automated pipetting workstation 420 as illustrated in FIG. 35.

Figure 36:
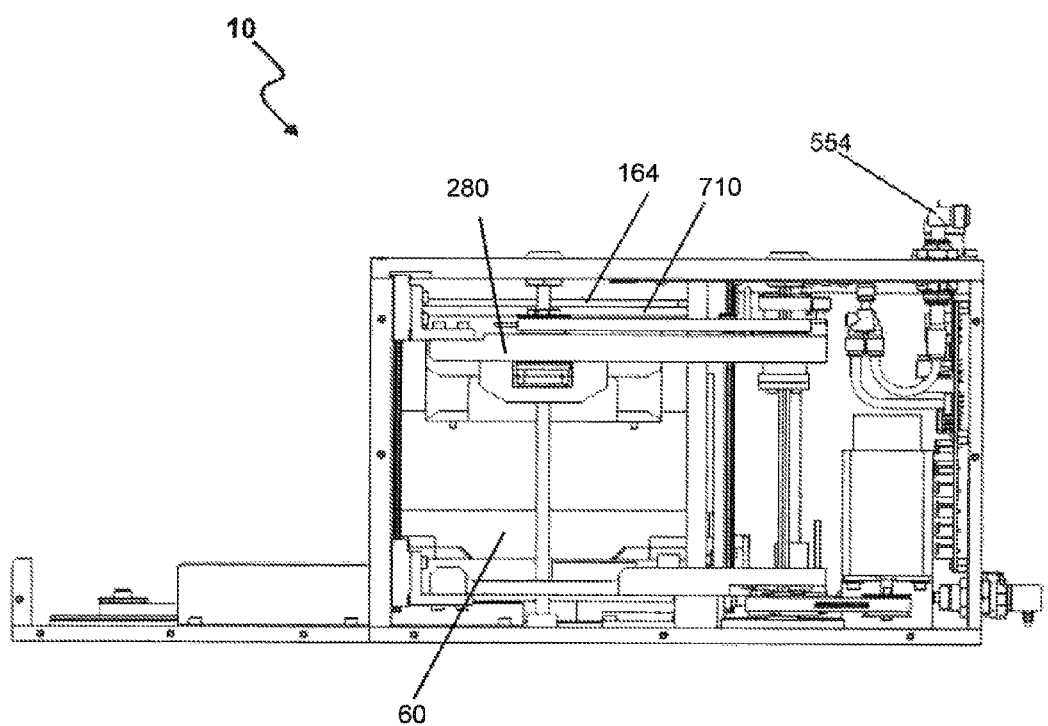
FIG. 36 is a front plan view of the automated positive pressure SPE apparatus shown presenting the evaporator adapter to the manifold with the upper elevator during the evaporation process.

Next, apparatus 10 then moves the evaporator adapter 710 to the manifold 164 via software control for presenting the evaporator adapter 710 to the manifold 164 with the upper elevator 280 as illustrated in FIG. 36.

Figure 37:
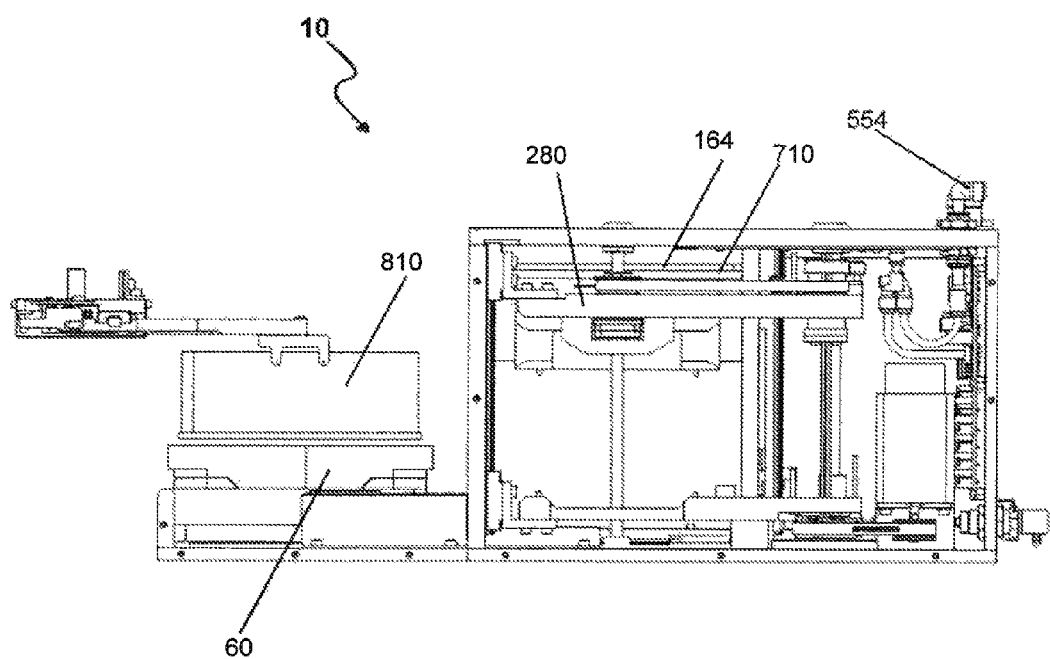
FIG. 37 is a front plan view of the automated positive pressure SPE apparatus shown presenting the shuttle assembly back to the automated pipetting workstation accessible position to allow the automated pipetting workstation to place the collection plate on the shuttle.

Apparatus 10 then moves the shuttle 60 to the automated pipetting workstation accessible position via software control for presenting the shuttle 60 back to the pipetting accessible position to allow the pipetter to place a collection plate 810 on the shuttle 60 as illustrated in FIG. 37.

Figure 38:
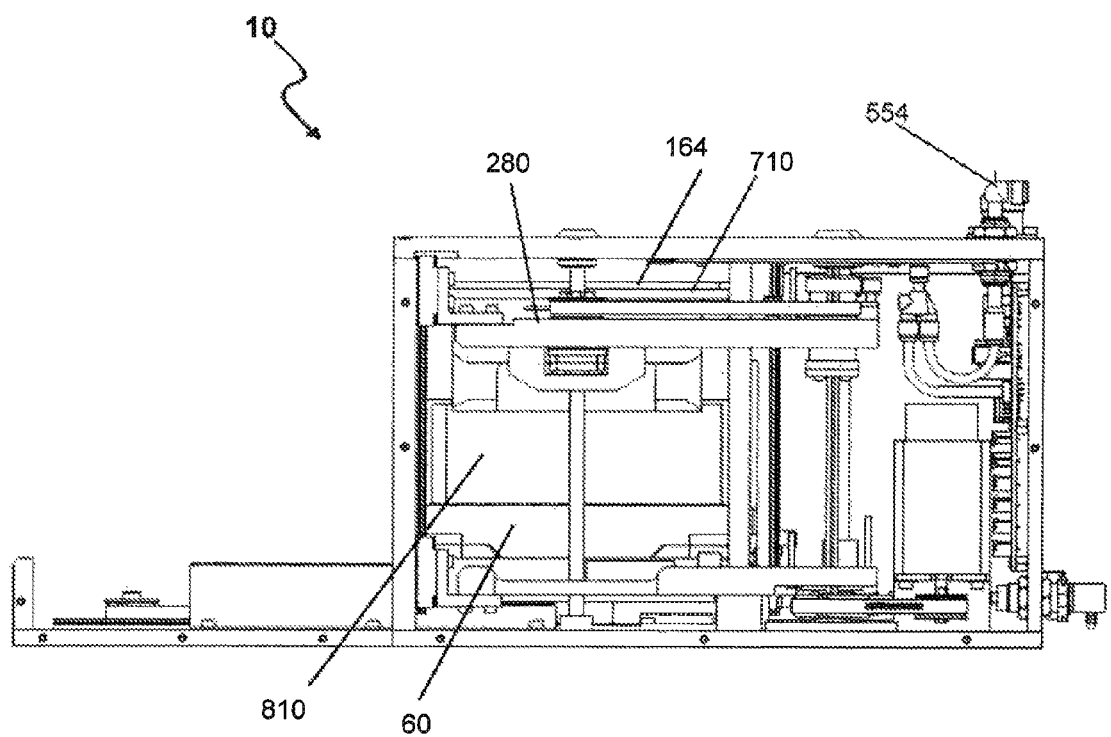
FIG. 38 is a front plan view of the automated positive pressure SPE apparatus shown presenting the shuttle assembly with the collection plate back to the lower elevator which will lift the collection plate to engage the needles of the evaporator adapter.
Figure 39:
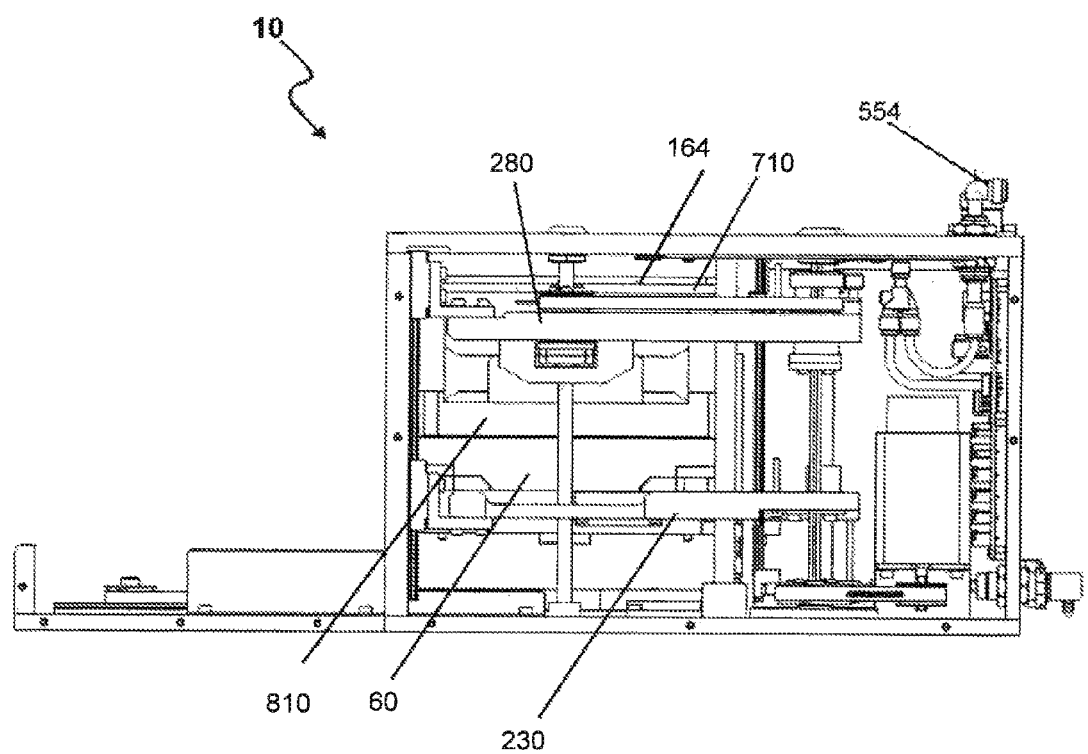
FIG. 39 is a front plan view of the automated positive pressure SPE apparatus shown with both the evaporator adapter and collection plate engaged.

As illustrated in FIGS. 38 and 39, and under software control, the collection plate 810 is then moved by the apparatus 10 for presenting the shuttle 60 with the collection plate 810 back to the lower elevator 230 which is then software controlled to lift the collection plate 810 to engage the needles of the evaporator adapter 710 just above the liquid height in the collection plate 810. Then, user specified heated air is applied to the liquid surface for a use specified time period to evaporate the liquid and leaving behind the solute.

Figure 40:
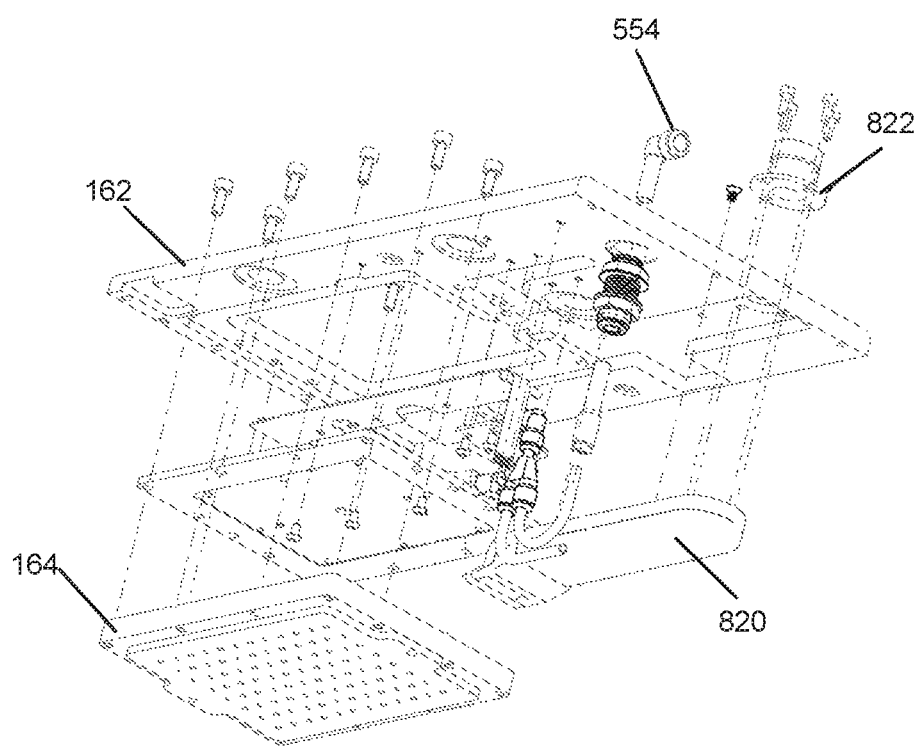
FIG. 40 is an exploded parts perspective view detailing a heater manifold assembly of the automated positive pressure SPE apparatus, the heater manifold assembly comprising a heater manifold unit housing a heater PCB and a plenum operatively coupled to a duct which is connected to the user's ventilation system.

Referring to FIG. 40, the evaporated vapors are directed through a plenum 820 to a duct 822 which is connected to the user's ventilation system. During the evaporation process, the lower tiered lift device 230 moves to keep the liquid being evaporated in close proximity to the evaporator adapter 710 to maximize efficiency of the evaporation process.

Figure 41:
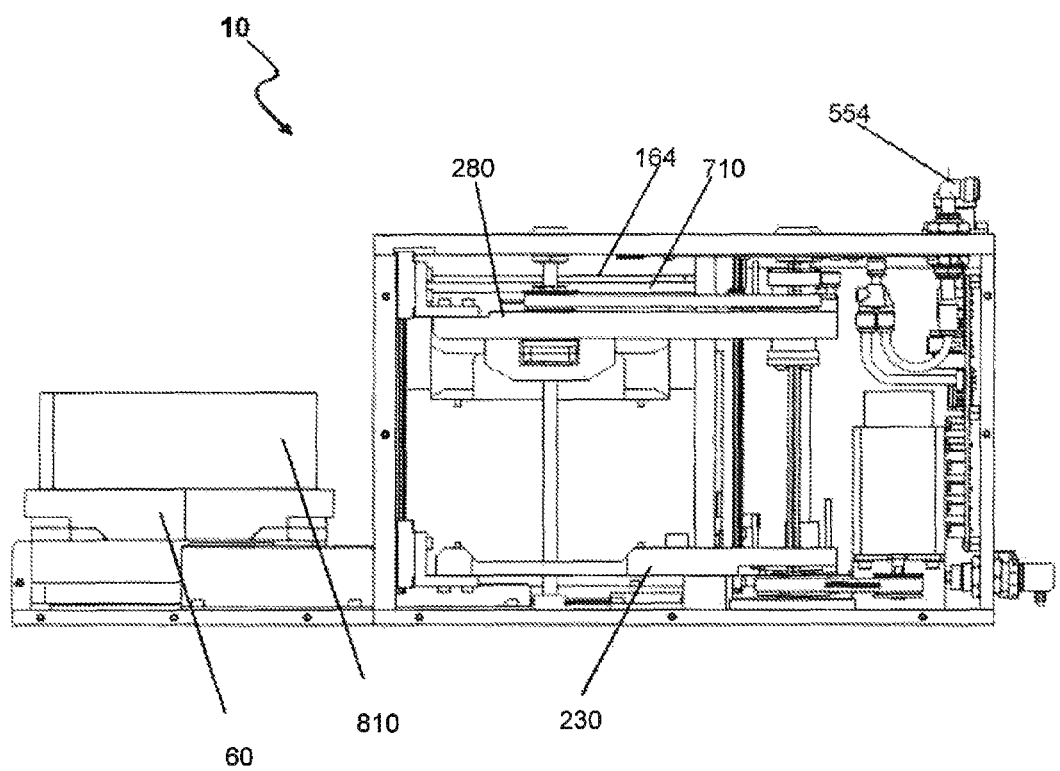
FIG. 41 is a front plan view of the automated positive pressure SPE apparatus shown presenting the collection plate back to the automated pipetting workstation accessible position to allow the automated pipetting workstation to remove the collection plate from the shuttle.

As illustrated in FIG. 41, apparatus 10 then moves the shuttle 60 with the collection plate 810 back to the pipette accessible position via software control for presenting the collection plate 810 back to the automated pipetting workstation accessible position for removal of the collection plate 810 from the shuttle 60 by the automated pipetting workstation 420 via software control.

Figure 42:
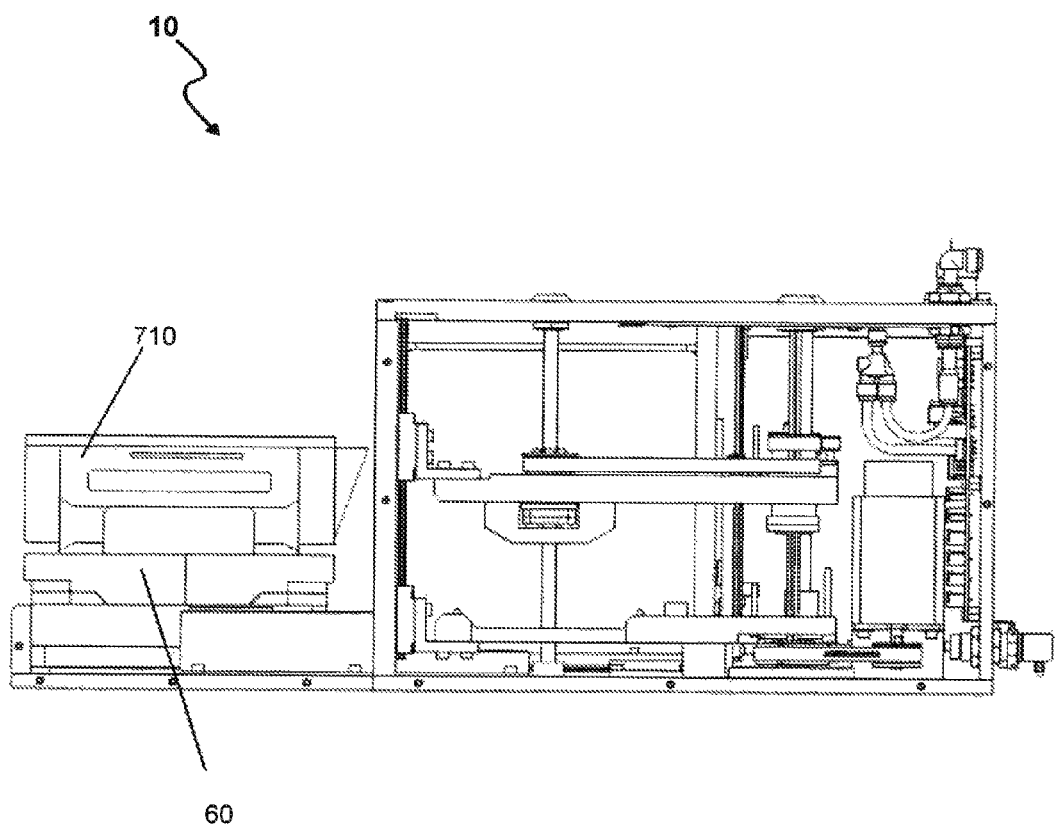
FIG. 42 is a front plan view of the automated positive pressure SPE apparatus shown presenting the evaporator adapter back to the automated pipetting workstation accessible position to allow the automated pipetting workstation to remove the evaporator adapter from the shuttle.

As illustrated in FIG. 42, apparatus 10 then collects the evaporator adapter 710 and moves the shuttle 60 with the evaporator adapter 710 back to the pipette accessible position via software control for presenting the evaporator adapter 710 back to the automated pipetting workstation accessible position for removal by the automated pipetting workstation 420 via software control.

Accordingly, the above delineated evaporation process comprises placing an evaporator adapter 710 onto the shuttle assembly 60 which presents the adapter 710 to the upper tiered lift device 280. The upper tiered lift device 280 presents the evaporator adapter 710 to the manifold plate 164 through which the apparatus controls both the flow via manifold pressure source assembly 550 and heat added via the heater control unit 700 to the system air.

Subsequently, this air flows through the evaporator adapter 710 into labware 810 which is presented to the adapter 710 by the lower tiered lift device 230. The labware 810 is presented in close proximity to the evaporator adapter 710 such that the controlled heated air is directed onto the liquid surface to be evaporated without the adapter 710 being in direct contact with the liquid being evaporated. The evaporated vapors are directed through the plenum 820 to the duct 822 which is connected to the user's ventilation system.

During the evaporation process, the lower tiered lift device 230 moves to keep the liquid being evaporated in close proximity to the evaporator adapter 710 to maximize efficiency of the evaporation process.

Process Security System 900

Figure 43:
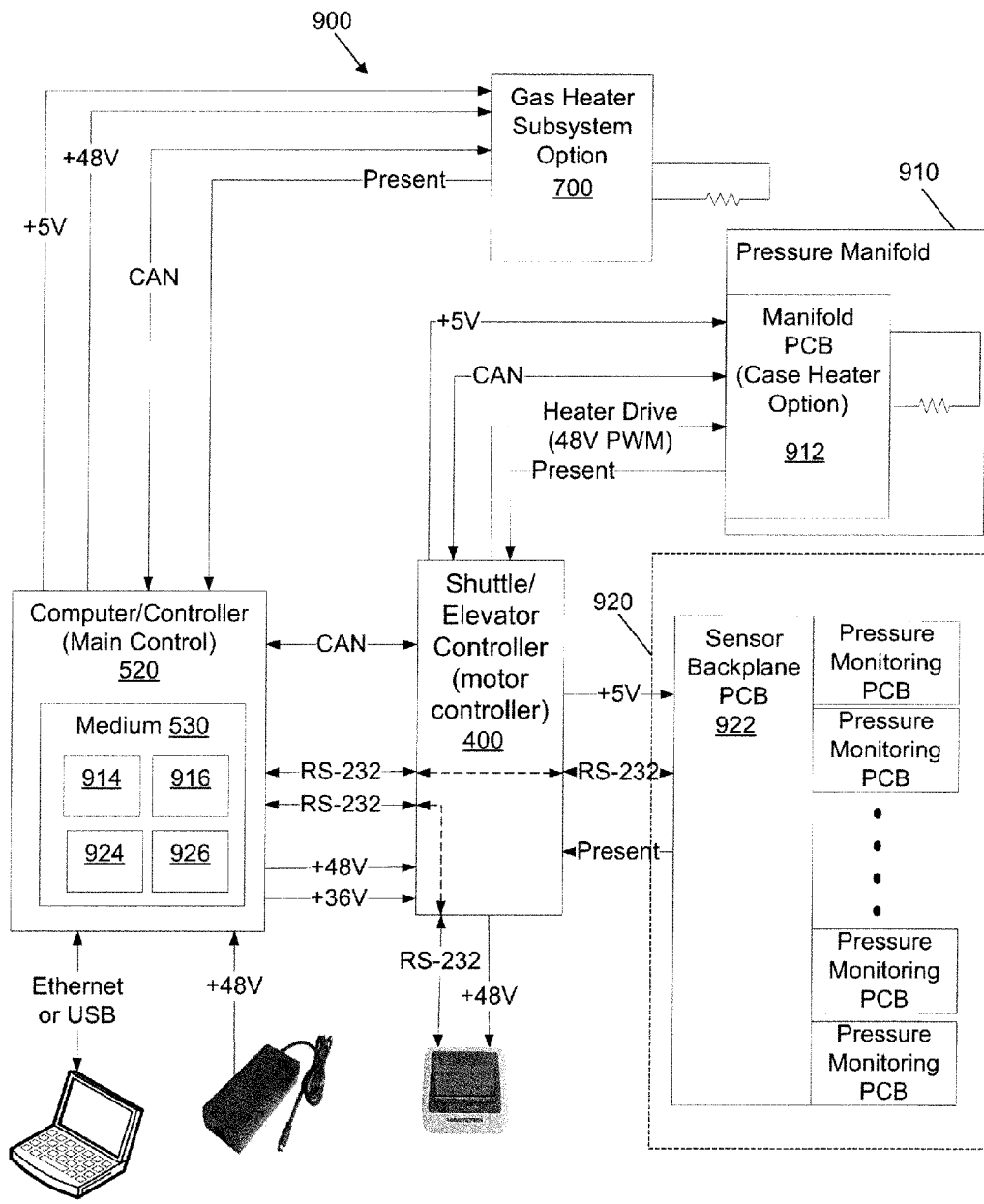
FIG. 43 is an electrical block diagram view of an embodiment of the automated positive pressure SPE system comprising a process security system comprised of pressure and temperature monitoring systems.

Referring to FIG. 43, and in another aspect, an embodiment of the automated positive pressure SPE apparatus 10 further comprises a process security system 900 for providing process security by use of a pressure sensor system 910 and a temperature sensor system 920 respectively comprising pressure sensors 912 and temperature sensors 922 that monitor the pressure and temperature change over time for an array of wells, for example up to 96 wells, during the SPE process.

The use of the pressure sensors 912 provides process security for each well of the labware by collecting pressure data which the process security system 900 utilizes to construct a curve 914 of the process utilizing computer/controller 520 delineated in detail above. This curve is then compared by the process security system 900 via computer/controller 520 to a previously stored standard acceptable curve 916 with tolerance boundaries defined from which a pass/error decision is made by the process security system 900 regarding the completeness and timeliness of the process being measured.

Typically, one or more standard acceptable curves 916 are stored in non-transitory computer-readable medium 530. The Errors are presented to the user and recorded permanently in a log file with time and date for traceability. The log file can also be stored in non-transitory computer-readable medium 530.

The temperature sensors 922 provide additional process security in applications that are sensitive to temperature variances by recording the temperature 924 of each well in the labware at various times during the process and having, for example, one or more bench mark temperatures 926 to which the recorded temperatures 924 are compared to for making decision. The one or more bench mark temperatures 926 and recorded temperatures 924 can be stored in non-transitory computer-readable medium 530.

Temperature values are also recorded permanently in a log file with date and time for traceability and future use. The log file can also be stored in non-transitory computer-readable medium 530. Errors are presented to the user and recorded permanently in the log file with time and date for traceability.

Tip Dryer

In another aspect, an embodiment of the invention provides an automated positive pressure SPE apparatus 10 that serves as a tip dryer by means of presenting a rack of tips to the upper tiered lift device 280 by the shuttle assembly 60. The upper tiered lift device 280 presents the rack of tips to the manifold plate through which the apparatus controls the flow of controlled heated air provided by heater control unit 700. Subsequently, this air flows through the individual tips and any liquid is captured by the shuttle assembly 60 and directed to a liquid waste container 564 (FIG. 32).

Cap Mat Sealing

In another aspect, an embodiment of the invention provides an automated positive pressure SPE apparatus 10 that serves as a cap mat sealing device. First, labware is place on the shuttle assembly 60. Then a cap mat is placed onto the top of the labware. The shuttle assembly 60 presents the stack to the upper tiered lift device. The upper tiered lift device presents the stack to the manifold plate and applies force as if attempting to seal the labware against the manifold plate 164 in the SPE process. This will seat the cap mat into the labware. Air pressure can be additionally applied to further seat the cap mat into the labware to create the necessary seal.

Lowering Profile Outboard Motor Positioning Assembly

Figure 44:
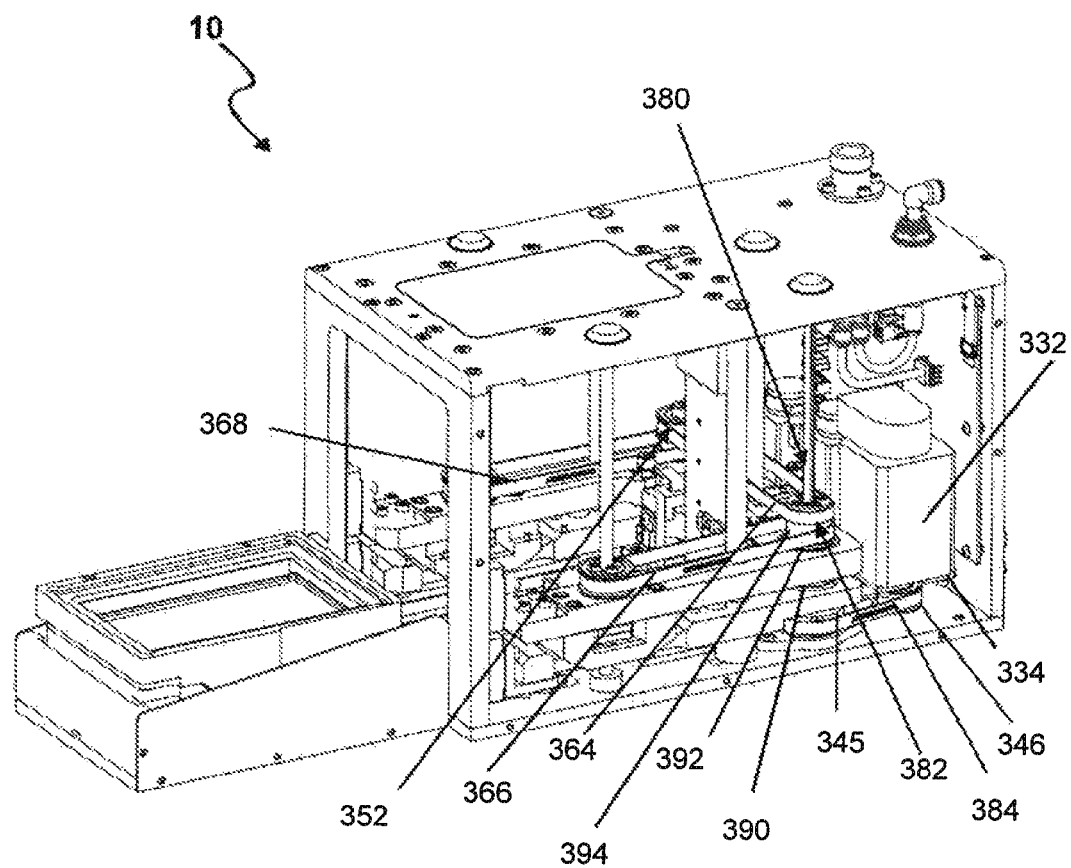
FIG. 44 is a forward lateral end and front longitudinal side perspective view of an embodiment of the positive pressure solid phase extraction (SPE) mechanism with lateral side plates removed there from for illustrating an elevator outboard location of the top elevator tier drive motor.
Figure 45:
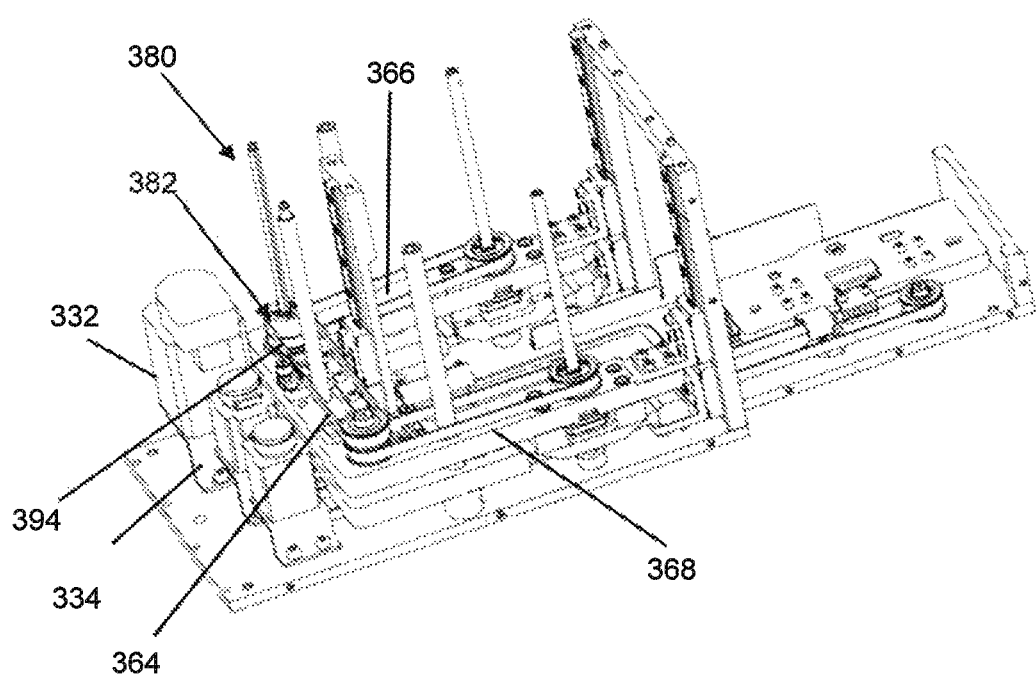
FIG. 45 is a top rear longitudinal view detailing the elevator outboard location of the top elevator tier drive, the bottom tier drive, the shuttle drive, and the tiered elevator lifts of the automated positive pressure SPE apparatus.
Figure 46:
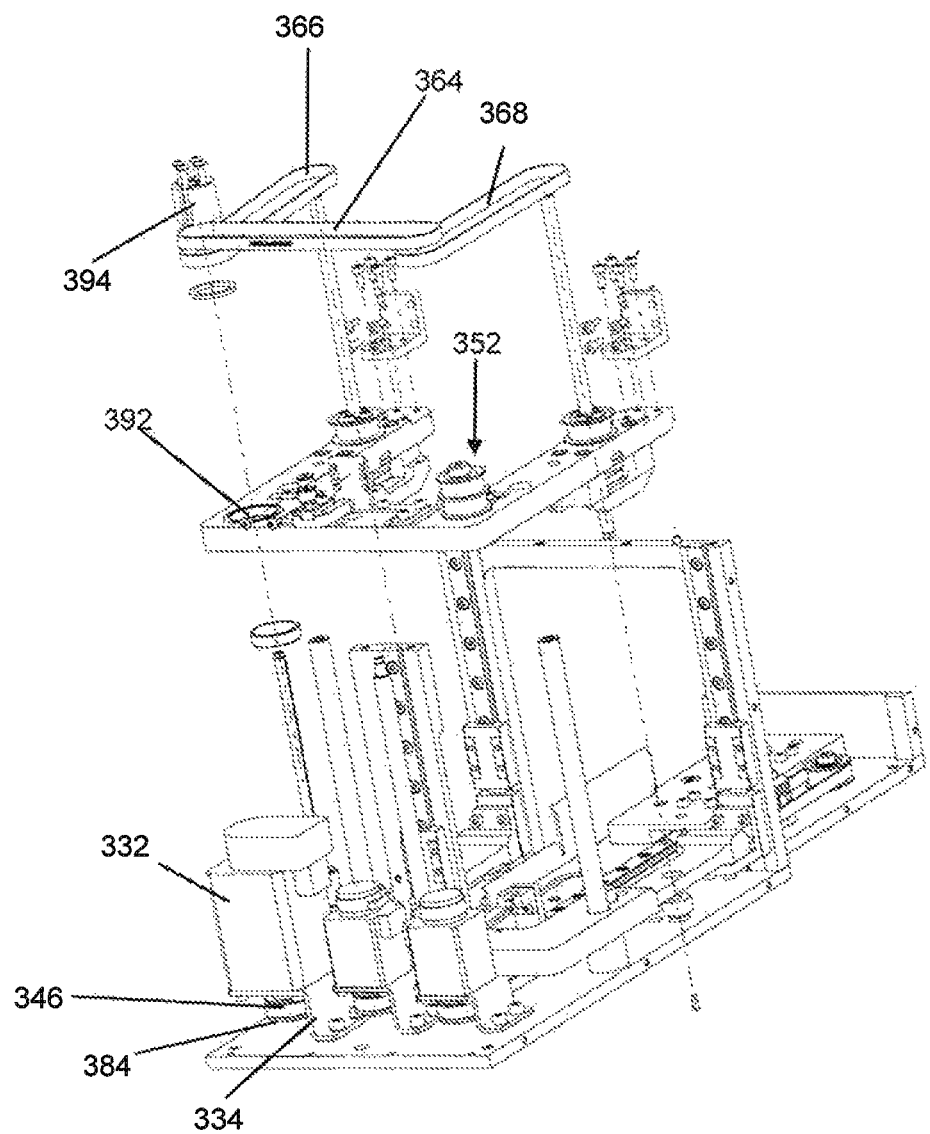
FIG. 46 is a top rear longitudinal partial exploded parts view further detailing a upper tiered lift belt assembly for the top elevator tier drive.

Referring to FIGS. 44 through 46, and in another aspect, an embodiment of the automated positive pressure SPE apparatus 10 further comprises disposing motor 332 outboard of the upper elevator lift 280 for lowering the height or profile of the apparatus 10.

In essence, the motor 332 and the supporting "U" shaped motor bracket 334 are moved off the upper elevator lift device 280 and posteriorly disposed from the posterior corner that latitudinally opposes the second cogged pulley assembly 352. The motor 332 is operatively coupled to the inferiorly disposed cogged pulley 346 at its outboard location.

In turn, a ball spline assembly 380 is provided having an inferiorly disposed pulley drive 382 coupled to a cogged pulley 345 operatively coupled to the cogged pulley 346 driven by reversibly excitable motor 332 via a belt 384.

The ball spline assembly 380 passes through the lower tiered lift device via aperture 390 and the upper tiered lift device via aperture 392.

Disposed above the upper tiered lift device is a bushing jacket spline 394 taking the place of assembly 342 at a complemental height with the belts 364, 366 operatively coupled thereto for rotation therewith when belt 384 is driven by motor 332 and wherein the rotation of belt 364 engenders the rotation of belt 368 via the second cogged pulley assembly 352 as detailed above.

The above delineation of the apparatus 10, including its use and operation, demonstrate the industrial applicability of this invention.

Accordingly, it should be apparent that further numerous structural modifications and adaptations may be resorted to without departing from the scope and fair meaning of the present invention as set forth hereinabove and as described herein below by the claims.

We claim:

1. An elevator lift, manifold, and shuttle assembly of an automated positive pressure solid phase extraction apparatus, said elevator lift, manifold, and shuttle assembly comprising:

an upper tiered lift device and a lower tiered lift device horizontally disposed in a vertical home position, wherein the upper tiered lift device is located in a first substantially horizontal plane a vertical distance above and over the lower tiered lift device;

a vertical framework;

a manifold plate configured to provide positive pressure when in contact with a labware and supported by said vertical framework in a second substantially horizontal plane vertically above said upper tiered lift device and said lower tiered lift device so as to define a vertically unobstructed elevator shaft in which said upper tiered lift device and said lower tiered lift device vertically travel;

means for individually vertically translating said upper tiered lift device and said lower tiered lift device in said vertically unobstructed elevator shaft between the vertical home position and a vertically elevated position below said manifold plate; and means for horizontally shuttling a shuttle supporting the labware into and out of said vertically unobstructed elevator shaft for presenting the labware to said upper tiered lift device and said lower tiered lift device for selectively vertically lifting the labware within said vertically unobstructed elevator shaft while selectively horizontally shuttling the shuttle out of and back into said vertically unobstructed elevator shaft.

2. An elevator lift, manifold, and shuttle assembly of an automated positive pressure solid phase extraction apparatus, said elevator lift, manifold, and shuttle assembly comprising:

a forked upper tiered lift device and a forked lower tiered lift device horizontally disposed at a vertical home position, wherein the upper tiered lift device is located in a first substantially horizontal plane a vertical distance above and over the lower tiered lift device;

a vertical framework;

a manifold plate configured to provide positive pressure when in contact with a labware and supported by said vertical framework in a second substantially horizontal plane vertically above said forked upper tiered lift device and said forked lower tiered lift device at the vertical home position so as to define a vertically unobstructed elevator shaft in which said forked upper tiered lift device and said forked lower tiered lift device vertically travel;

means for individually vertically translating said forked upper tiered lift device and said forked lower tiered lift device in said vertically unobstructed elevator shaft defined by said vertical framework supporting said manifold plate; and means for horizontally shuttling a shuttle supporting the labware into said vertically unobstructed elevator shaft vertically below said manifold plate for presenting the labware to said forked upper tiered lift device and said forked lower tiered lift device for selectively vertically lifting the labware within said vertically unobstructed elevator shaft and selectively horizontally shuttling the shuttle out of said vertically unobstructed elevator shaft vertically clear of said manifold plate.

* * * * *